US011660025B2

(12) United States Patent
Ariyama et al.

(10) Patent No.: US 11,660,025 B2
(45) Date of Patent: May 30, 2023

(54) IDENTIFICATION DEVICE, IDENTIFICATION METHOD, AND RECORDING MEDIUM WITH RECORDED IDENTIFICATION PROGRAM

(71) Applicant: NEC Corporation, Tokyo (JP)

(72) Inventors: Tetsuri Ariyama, Tokyo (JP); Terumi Umematsu, Tokyo (JP); Yuji Ohno, Tokyo (JP); Katsumi Abe, Tokyo (JP); Mineto Satoh, Tokyo (JP); Takeshi Akagawa, Tokyo (JP); Masahiro Kubo, Tokyo (JP); Tan Azuma, Tokyo (JP); Kenichiro Fujiyama, Tokyo (JP); Soichiro Araki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 567 days.

(21) Appl. No.: 16/629,080

(22) PCT Filed: Jul. 11, 2017

(86) PCT No.: PCT/JP2017/025215
§ 371 (c)(1),
(2) Date: Jan. 7, 2020

(87) PCT Pub. No.: WO2019/012597
PCT Pub. Date: Jan. 17, 2019

(65) Prior Publication Data
US 2020/0196912 A1 Jun. 25, 2020

(51) Int. Cl.
*A61B 5/117* (2016.01)
*A61B 5/02* (2006.01)
(Continued)

(52) U.S. Cl.
CPC .............. *A61B 5/117* (2013.01); *G06F 21/32* (2013.01); *A61B 5/02035* (2013.01); *A61B 5/0295* (2013.01)

(58) Field of Classification Search
CPC ................ A61B 5/117; A61B 5/02035; A61B 5/0295; G06F 21/32
See application file for complete search history.

(56) References Cited

U.S. PATENT DOCUMENTS

2005/0053264 A1 3/2005 Amano et al.
2012/0253154 A1 10/2012 Phillips et al.
(Continued)

FOREIGN PATENT DOCUMENTS

JP H10-258038 A 9/1998
JP 2004-089675 A 3/2004
(Continued)

OTHER PUBLICATIONS

International Search Report for PCT Application No. PCT/JP2017/025215, dated Aug. 29, 2017.
(Continued)

*Primary Examiner* — Kwin Xie

(57) ABSTRACT

An identification device including a generation unit and an information identification unit. The generation unit generates factor information relating to pulse-wave information with respect to an identification target in accordance with biological model information representing a relevance between pulse-wave information representing a pulse wave and the factor information representing a factor of pulse wave. The information identification unit selects certain list information satisfying a predetermined determination criterion of the factor information generated by the generation unit out of list information associating the factor information generated based on the pulse-wave information representing a pulse wave of a biological subject to be an identification target with identification information for identifying the biological subject, and identifies the identification information in the selected certain list information.

13 Claims, 13 Drawing Sheets

(51) Int. Cl.

| | |
|---|---|
| ***G06F 21/32*** | (2013.01) |
| *A61B 5/0295* | (2006.01) |

(56) References Cited

U.S. PATENT DOCUMENTS

| | | | | |
|---|---|---|---|---|
| 2015/0359486 | A1* | 12/2015 | Kovacs | G01G 19/50 600/301 |
| 2017/0146386 | A1* | 5/2017 | Wiard | G16Z 99/00 |
| 2017/0148240 | A1* | 5/2017 | Kovacs | G01G 23/36 |
| 2017/0173262 | A1* | 6/2017 | Veltz | G16H 20/17 |
| 2018/0106897 | A1* | 4/2018 | Shouldice | A61B 5/4812 |

FOREIGN PATENT DOCUMENTS

| | | | |
|---|---|---|---|
| JP | 2004-173826 | A | 6/2004 |
| JP | 2006-218033 | A | 8/2006 |
| JP | 2009-247733 | A | 10/2009 |
| JP | 2010-110380 | A | 5/2010 |
| JP | 2011-072674 | A | 4/2011 |
| JP | 2012187300 | A | 10/2012 |
| JP | 2016-120212 | A | 7/2016 |
| JP | 2016-214519 | A | 12/2016 |

OTHER PUBLICATIONS

English translation of Written opinion for PCT Application No. PCT/JP2017/025215.
Japanese Office Action for JP Application No. 2019-529350 dated Aug. 18, 2020 with English Translation.
Japanese Office Action for JP Application No. 2020-174098 dated Aug. 10, 2021 with English Translation.

* cited by examiner

IDENTIFICATION DEVICE
101
GENERATION UNIT
102
INFORMATION IDENTIFICATION UNIT
103
LIST INFORMATION STORAGE UNIT
150

START
GENERATE FACTOR INFORMATION RELATING TO PULSE-WAVE INFORMATION
S101
SELECT LIST INFORMATION SATISFYING PREDETERMINED DETERMINATION CRITERION
S102
IDENTIFY IDENTIFICATION INFORMATION
S103
END

PULSE WAVE
(A)
ORIGIN
TIME
31
32
33
34
35
36
37
PULSE WAVE
(B)
ORIGIN
TIME
41
42
43

211
PULSE-WAVE MEASUREMENT UNIT
212
ENVIRONMENT INFORMATION OBTAINMENT UNIT
201
IDENTIFICATION DEVICE
202
FILTER PROCESSING UNIT
102
GENERATION UNIT
203
INFORMATION IDENTIFICATION UNIT
213
DISPLAY UNIT
214
BIOLOGICAL INFORMATION STORAGE UNIT
150
LIST INFORMATION STORAGE UNIT

START
PULSE-WAVE INFORMATION INCLUDES NOISE?
S201
NO
YES
REMOVE NOISE
S202
GENERATE FACTOR INFORMATION RELATING TO PULSE-WAVE INFORMATION
S101
SELECT LIST INFORMATION SATISFYING PREDETERMINED DETERMINATION CRITERION
S203
IDENTIFY IDENTIFICATION INFORMATION
S204
END

Fig.9

| BIOLOGICAL INFORMATION | | | | | | | | | |
|---|---|---|---|---|---|---|---|---|---|
| IDENTIFICATION INFORMATION | MEASUREMENT DATE AND TIME | WATER INFORMATION | PRESSURE INFORMATION | HEART RATE | HIGHEST BLOOD PRESSURE | LOWEST BLOOD PRESSURE | DOSING INFORMATION | PULSE WAVE ID | ... |
| A | 2016/5/2 8:30 | 0 | — | 58 | 140 | 80 | MA | A1 | ... |
| B | 2017/3/3 10:12 | 100 | — | 63 | 120 | 70 | MB | B2 | ... |
| C | 2016/9/5 5:40 | 0 | — | 61 | 130 | 80 | MC | C3 | ... |
| ... | ... | ... | ... | ... | ... | ... | ... | ... | ... |

START
S301
EXTRACT EJECTION WAVE AND REFLECTED WAVE IN PULSE WAVE
S302
CALCULATE TIME DIFFERENCE BETWEEN EJECTION WAVE AND REFLECTED WAVE
S303
IDENTIFY TIME DIFFERENCE SATISFYING PREDETERMINED DETERMINATION CRITERION
S304
IDENTIFY IDENTIFICATION INFORMATION
END

351
HEART
352
353
354

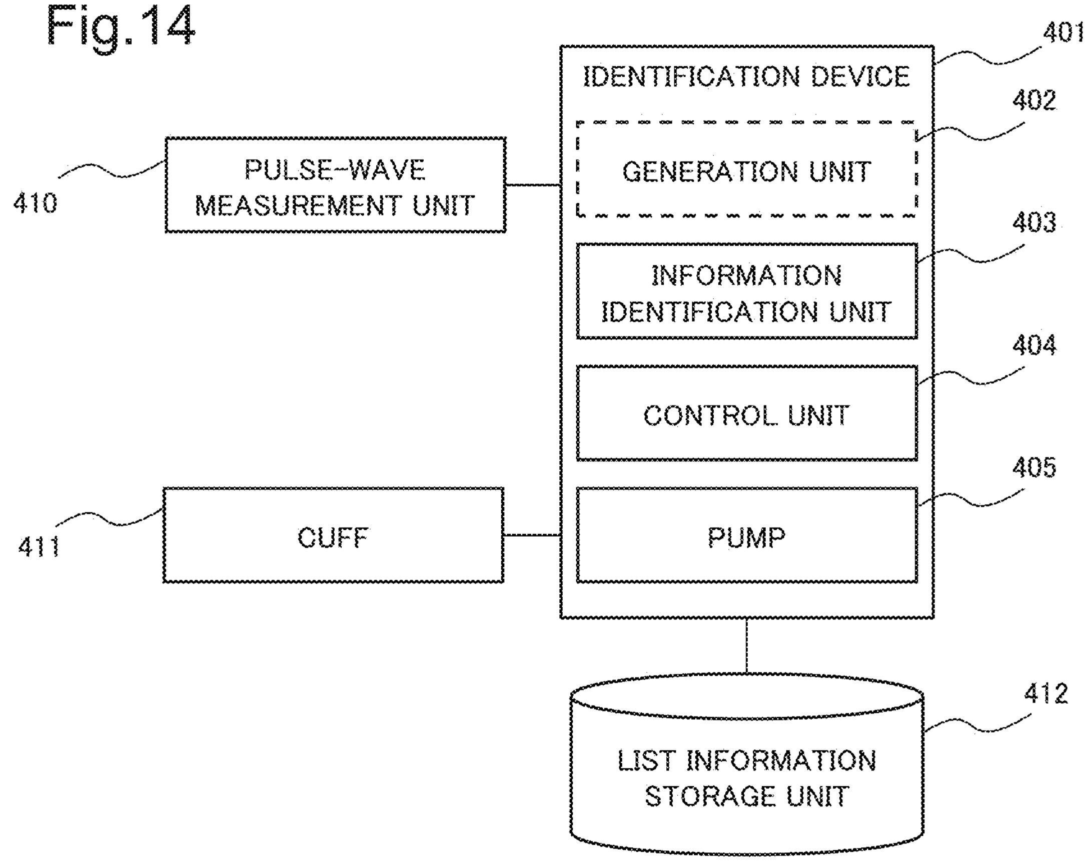
Fig.14
IDENTIFICATION DEVICE
401
GENERATION UNIT
402
PULSE-WAVE MEASUREMENT UNIT
410
INFORMATION IDENTIFICATION UNIT
403
CONTROL UNIT
404
CUFF
411
PUMP
405
LIST INFORMATION STORAGE UNIT
412

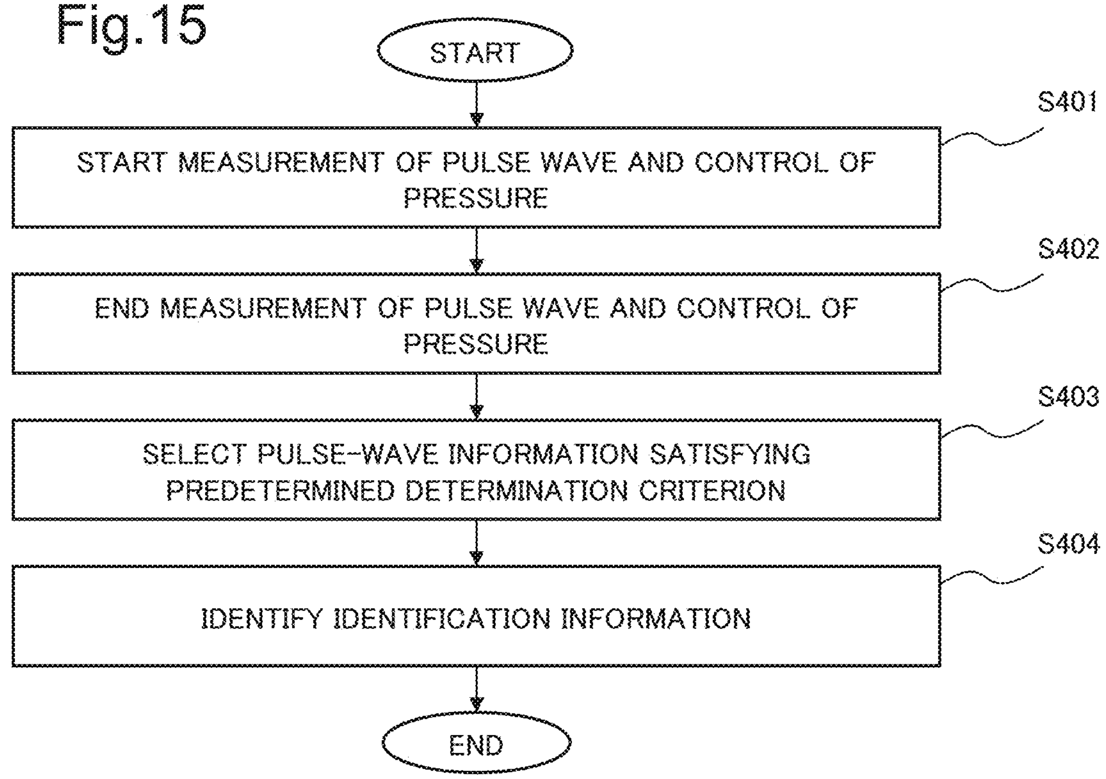
Fig.15
START
START MEASUREMENT OF PULSE WAVE AND CONTROL OF PRESSURE
S401
END MEASUREMENT OF PULSE WAVE AND CONTROL OF PRESSURE
S402
SELECT PULSE-WAVE INFORMATION SATISFYING PREDETERMINED DETERMINATION CRITERION
S403
IDENTIFY IDENTIFICATION INFORMATION
S404
END 20
CALCULATION PROCESSING DEVICE
CPU
21
MEMORY
22
DISK
23
NON-VOLATILE RECORDING MEDIUM
24
COMMUNICATION IF
27
OUTPUT DEVICE
26
INPUT DEVICE
25

IDENTIFICATION DEVICE, IDENTIFICATION METHOD, AND RECORDING MEDIUM WITH RECORDED IDENTIFICATION PROGRAM

This application is a National Stage Entry of PCT/JP2017/025215 filed on Jul. 11, 2017, the contents of all of which are incorporated herein by reference, in their entirety.

TECHNICAL FIELD

The present invention relates to a biometric identification device and the like, based on biological information.

BACKGROUND ART

Information relating to a biological pulse wave is used in, for example, techniques described in PTLs 1 to 3.

PTL 1 discloses a collation device which determines an operator, based on a fingerprint of the operator, and a pulse wave of the operator. The collation device determines, based on the fingerprint, whether an operator is the operator himself/herself. When the operator is determined to be the operator himself/herself, the collation device determines, based on the pulse wave, whether the operator is alive, and when determining that the operator is alive, the collation device determines that the operator is genuine.

PTL 2 discloses an estimation device which estimates a state of blood vessels. The estimation device detects a pulse wave using a photosensor, executes differential processing for the detected pulse wave, and calculates, based on the calculated result, a characteristic point relating to the pulse wave. The estimation device estimates a state of blood vessels, based on a difference of timings at which a characteristic point appears.

PTL 3 discloses an identification device which identifies a biological subject, based on pulse-wave information. The identification device generates an acceleration pulse wave representing acceleration when a pulse wave measured in a biological subject varies, and identifies the biological subject, based on amplitude in the generated acceleration pulse wave.

Furthermore, PTL 4 discloses an identification device which authenticates an individual, based on waveform data of Korotkoff sound. PTL 5 discloses a blood pressure meter which determines whether the local device is appropriately used. When an operation of starting blood pressure of a measurement target is performed, the blood pressure meter captures an image of a face of the measurement target, and a cuff attached to the measurement target, and calculates, based on the captured image, a position of the cuff, a position of the face, a direction of the cuff, and a direction of the face. When the face is at a position higher than the cuff, and the face and the cuff are in the same direction, the blood pressure meter starts measurement of blood pressure.

CITATION LIST

Patent Literature

[PTL 1] Japanese Unexamined Patent Application Publication No. 2004-089675

[PTL 2] Japanese Unexamined Patent Application Publication No. 2011-072674

[PTL 3] Japanese Unexamined Patent Application Publication No. 2006-218033

[PTL 4] Japanese Unexamined Patent Application Publication No. 2010-110380

[PTL 5] Japanese Unexamined Patent Application Publication No. 2009-247733

SUMMARY OF INVENTION

Technical Problem

A pulse wave measured biologically differs from biological subject to biological subject. However, biometric identification is not possible even by using either of the devices disclosed in PTLs 1 and 2. A reason for this is that either of the devices does not have a function of biometric identification, based on a pulse wave measured biologically. Moreover, biometric identification is not necessarily possible correctly even by using the identification device disclosed in PTL 3. A reason for this is that an acceleration pulse wave used in the identification device is easily affected by noise included in a pulse wave. Moreover, it is not necessarily possible to correctly identify a biological subject even by using the identification device disclosed in PTL 4.

Thus, one object of the present invention is to provide an identification device and the like being capable of correctly identifying an identification target.

Solution to Problem

As one aspect of the present invention, an identification device includes:

a generation unit that generates factor information relating to pulse-wave information with respect to an identification target in accordance with biological model information representing a relevance between pulse-wave information representing a pulse wave and the factor information representing a factor of pulse wave; and an information identification unit that selects certain list information satisfying a predetermined determination criterion of the factor information generated by the generation unit out of list information associating the factor information generated based on the pulse-wave information representing a pulse wave of a biological subject to be an identification target with identification information for identifying the biological subject, and identifies the identification information in the selected certain list information.

Further, as another aspect of the present invention, an identification method by an information processing device, the identification method includes:

generating factor information relating to pulse-wave information with respect to an identification target in accordance with biological-model information representing a relevance between pulse-wave information representing a pulse wave and the factor information representing a factor of pulse wave;

selecting certain list information satisfying a predetermined determination criterion of the generated factor information out of list information associating the factor information generated based on the wave information representing a pulse wave of a biological subject to be an identification target with identification information for identifying the biological subject; and identifying the identification information in the selected certain list information.

Further, as still another aspect of the present invention, an identification program causes a computer to achieve:

a generation function of generating factor information relating to pulse-wave information with respect to an identification target in accordance with biological-model information representing a relevance between pulse-wave information representing a pulse wave and the factor information representing a factor of pulse wave; and an information identification function of selecting certain list information satisfying a predetermined determination criterion of the generated factor information out of list information associating the factor information generated based on the wave information representing a pulse wave of a biological subject to be an identification target with identification information for identifying the biological subject, and identifying the identification information in the selected certain list information.

Furthermore, the object is also achieved by a computer-readable recording medium recording the program.

Advantageous Effects of Invention

An identification device and the like according to the present invention can correctly identify an identification target.

BRIEF DESCRIPTION OF DRAWINGS

FIG. 9 is a diagram conceptually representing one example of biological information.

FIG. 14 is a block diagram illustrating a configuration included in an identification device according to a fourth example embodiment of the present invention.

FIG. 15 is a flowchart illustrating an operation in the identification device according to the fourth example embodiment.

EXAMPLE EMBODIMENT

Next, example embodiments of the present invention will be described in detail with reference to the drawings.

First Example Embodiment

Figure 1:
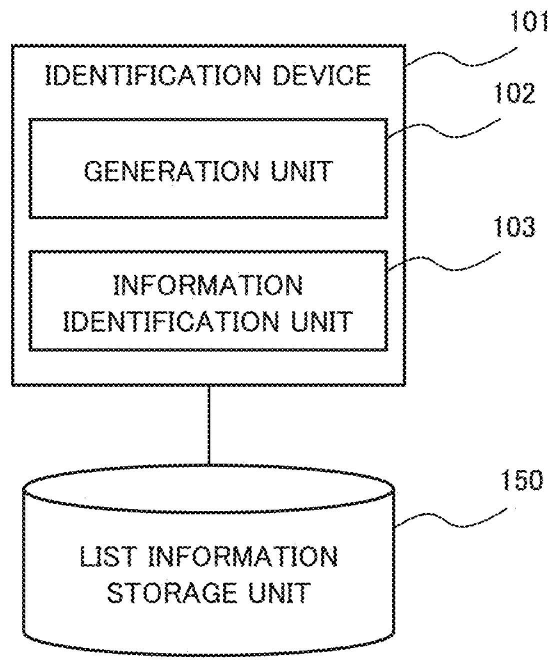
FIG. 1 is a block diagram illustrating a configuration included in an identification device according to a first example embodiment of the present invention.

A configuration included in an identification device 101 according to a first example embodiment of the present invention is described in detail with reference to FIG. 1. FIG. 1 is a block diagram illustrating a configuration included in the identification device 101 according to the first example embodiment of the present invention.

The identification device 101 according to the first example embodiment includes a generation unit 102 and an information identification unit 103.

It is assumed that the identification device 101 is communicably connected to a list information storage unit 150. The identification device 101 may include the list information storage unit 150.

Figure 4:
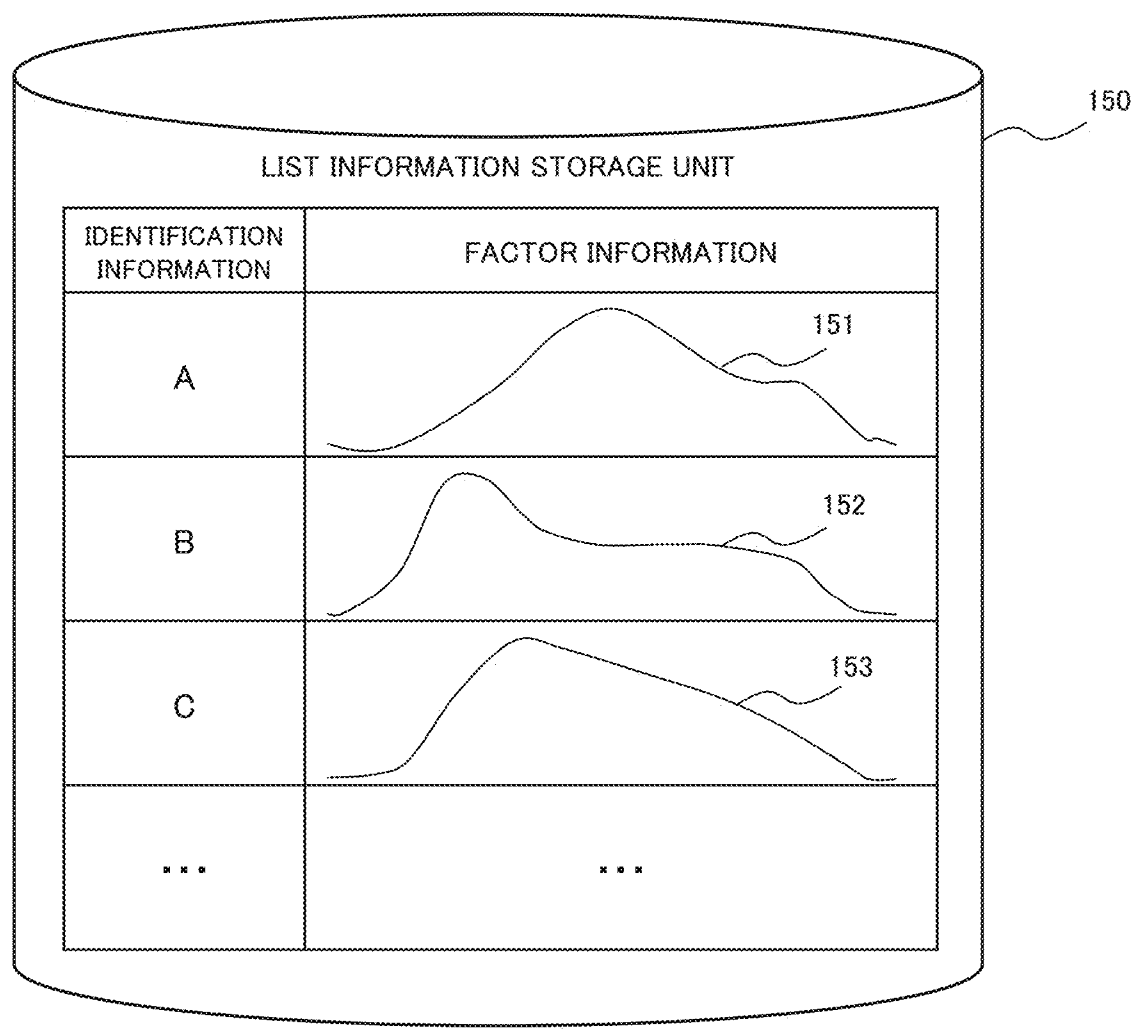
FIG. 4 is a diagram conceptually representing one example of list information stored in a list information storage unit.

The list information storage unit 150 (exemplified in FIG. 4) stores list information associating factor information (factor information 151, factor information 152, factor information 153, and the like) generated by the generation unit 102 in relation to a biological subject, with identification information representing an identifier being capable of uniquely identifying the biological subject. FIG. 4 is a diagram conceptually representing one example of list information stored in the list information storage unit 150. A method of generating factor information will be described later with reference to Equations 1 to 3 and the like.

In list information exemplified in FIG. 4, for example, identification information "A" is associated with the factor information 151. This represents that factor information generated based on pulse-wave information measured in a biological subject represented by the identification information "A" is the factor information 151. The list information may further include different information, and is not limited to the example described above. Herein, factor information generated by the generation unit 102 is described.

Factor information represents information generated in accordance with processing described later with reference to FIG. 2, based on pulse-wave information representing a pulse wave of a biological subject. The factor information is, for example, information representing a change in a state of blood vessels in the biological subject, a change in a state of blood in the blood vessels, a change in a volume of blood flow, or a change in a state of blood flow. Factor information may be estimation information estimating these changes. Moreover, in the list information exemplified in FIG. 4, factor information is represented as continuously changing information, but may be discretely represented information. When factor information is discretely represented information, the factor information is a value representing a state (or a change or the like of a state) at at least one timing.

Factor information is, for example, blood vessel resistance representing an occlusion degree of blood flow in blood vessels. Blood vessel resistance is caused in, for example, capillary blood vessels, peripheral blood vessels, or the like. Factor information is, for example, a volume of blood flow in blood vessels. Blood flow is caused by an outflow of blood from a heart, or the like. Factor information is, for example, viscosity of blood (hereinafter, represented as "blood viscosity"). Blood viscosity changes according to a volume of red blood cells included in blood, a shape of a blood cell, viscosity of blood plasma, and the like. Factor information may be, for example, information representing elasticity of blood vessels, or may be a cardiac outflow volume representing a volume of blood flow flowing out from a heart. Factor information has only to be information representing blood vessels, or a change relating to blood, and is not limited to the example described above.

Next, pulse-wave information is described.

Pulse-wave information is information representing a pulse wave of an identification target (or a biological subject). For example, pulse-wave information may be information (exemplified in (A) of FIG. 3) representing a pulse wave measured in a period in which a part of the identification target such as an arm, a wrist, or the like is pressured, or may be information (exemplified in (B) of FIG. 3) representing a pulse wave measured in a period in which the identification target is not externally pressured. Alternatively, pulse-wave information may include both a pulse wave measured in a period in which a part of the biological subject is pressured, and a pulse wave measured in a period in which the biological subject is not pressured.

Figure 3:
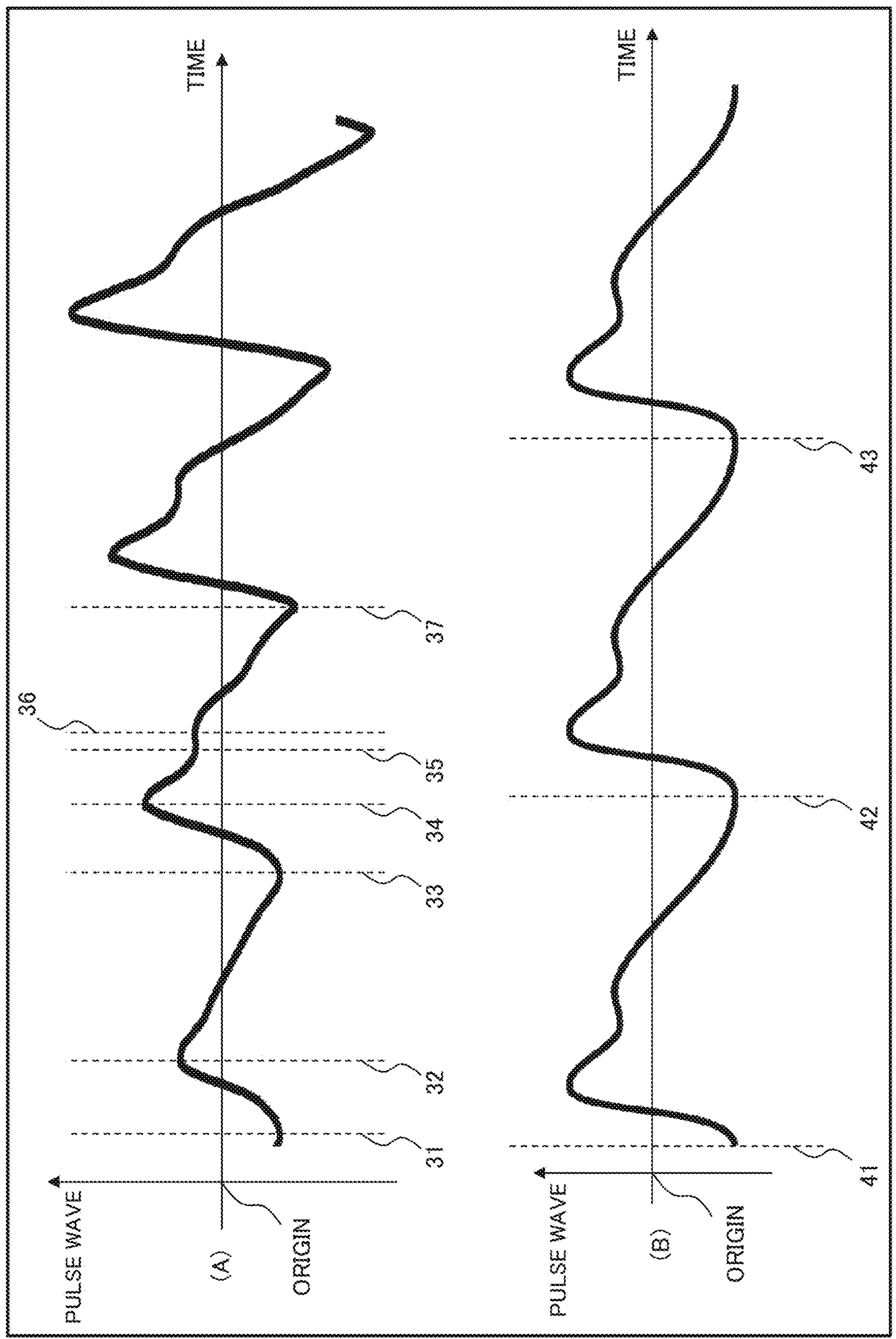
FIG. 3 is a diagram conceptually representing one example of pulse-wave information.

(A) of FIG. 3 is a diagram conceptually representing one example of pulse-wave information measured in a period in which a part of a biological subject is pressured. (B) of FIG. 3 is a diagram conceptually representing one example of pulse-wave information measured in a period in which the pressure is not externally applied. A horizontal axis in each of (A) and (B) of FIG. 3 represents time, and represents that time elapses toward a right side. A vertical axis in each of (A) and (B) of FIG. 3 represents a size of a pulse wave, and represents that a pulse wave is larger as distance upwardly or downwardly increases from an origin. Timings 31 to 37 illustrated in (A) of FIG. 3, and timings 41 to 43 illustrated in (B) of FIG. 3 will be described later in a fourth example embodiment.

Pressure (external pressure) applied to an identification target (or a biological subject) may not have to be constant, and, for example, may increase as time elapses, or may decrease as time elapses. Alternatively, as seen in general blood pressure meters, the pressure may increase in a period before a highest blood pressure is measured, and may decrease after the highest blood pressure is measured. Pressure has only to be controlled in accordance with a predetermined pressure control procedure, and is not limited to the example described above.

Next, processing in the identification device 101 according to the first example embodiment of the present invention is described in detail with reference to FIG. 2. FIG. 2 is a flowchart illustrating flow of processing in the identification device 101 according to the first example embodiment.

The generation unit 102 receives pulse-wave information (exemplified in FIG. 3) representing a pulse wave of an identification target. The pulse-wave information is, for example, information representing a pulse wave of the identification target in a certain period. The generation unit 102 generates factor information representing a parameter adapted to the pulse-wave information, in accordance with biological-model information (described later with reference to Equations 1 and 2) in which a relevance among states of an identification target (or a biological subject) is represented using parameters at a plurality of timings (step S101).

The information identification unit 103 selects, out of list information (exemplified in FIG. 4) stored in the list information storage unit 150, list information in which factor information in the list information and factor information generated by the generation unit 102 satisfy a predetermined determination criterion (described later) (step S102). The information identification unit 103 identifies identification information representing an identifier included in the selected list information (exemplified in FIG. 4) (step S103).

Biological-model information is described with reference to Equations 1, 2, and the like. Biological-model information is a model representing a relevance among states of a biological subject (or an identification target) at a plurality of timings. Biological-model information is, for example, information representing a relevance between a state of a biological subject at a first timing, and a state of the biological subject at a second timing. A state is, for example, blood-vessel internal pressure representing a level of pressure inside blood vessels in a biological subject. The first timing and the second timing may be different from each other. Hereinafter, for convenience of description, it is supposed that a state represents blood-vessel internal pressure. However, a state is not limited to blood-vessel internal pressure, and may be, for example, information representing a size of a pulse wave.

Biological-model information is, for example, model information as exemplified in Equations 1 and 2.

$$X_t=(x_t,\theta_t)=g(x_{t-1},\theta_t)+v_t \quad \text{(Equation 1)},$$

$$y_t=h(x_t)+w_t \quad \text{(Equation 2)}.$$

However, t represents a timing. $x_t$ represents a state (e.g., blood-vessel internal pressure) of a biological subject at a timing t. $y_t$ represents measurement information (e.g., a size of a pulse wave) measured in relation to a biological subject. The measurement information may be pulse pressure. Measurement information is measured by use of, for example, a pressure sensor, a photoelectric sensor, a photosensor, an ultrasonic sensor, a sound wave sensor, an electric field sensor, a magnetic field sensor, an imaging device, a vibration sensor, or the like. A parameter θ represents a value of a parameter used in processing of calculating a state at the timing t, from a state at a timing (t−1). $v_t$ represents an error relating to processing g. $w_t$ represents an error relating to h.

The processing g exemplified in Equation 1 conceptually represents, for example, processing of solving a differential equation exemplified in Equation 3, in relation to a variable x.

$$m\frac{d^2x}{dt^2}=-kx-c\frac{dx}{dt}+F \quad \text{(Equation 3)}$$

However, m represents a volume of blood flow. k represents blood vessel resistance. c represents blood viscosity. F represents force applied to blood vessels. The force F represents, for example, force generated by a heartbeat. Blood is caused to flow out from a heart according to a heartbeat, and a pulse wave generates a factor of force F by blood which is caused to flow out. When it is supposed that force with which a heart beats is an impulse input, it can also be considered that a pulse wave represents an impulse response according to the impulse input. x represents blood-vessel internal pressure, and corresponds to a state x (e.g., $x_t$, $x_{t-1}$, or the like) in Equation 1.

Figure 5:
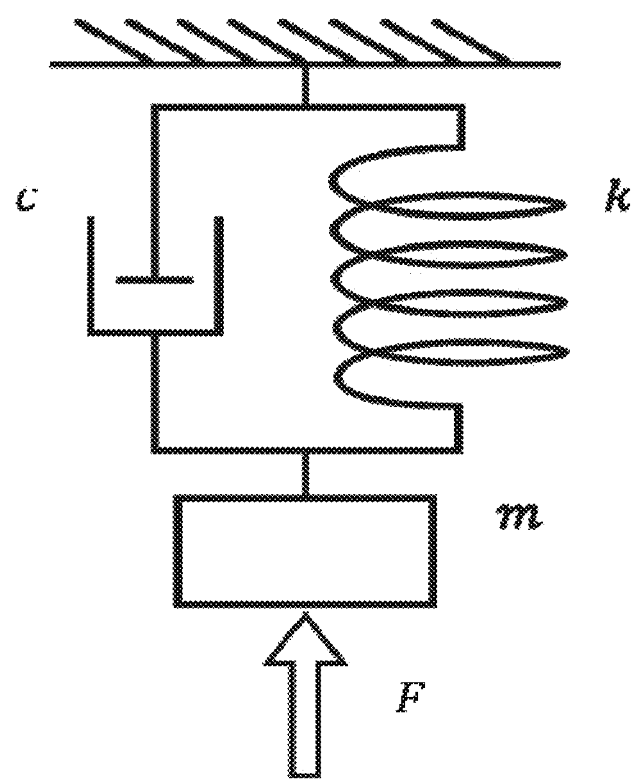
FIG. 5 is a diagram conceptually representing one example of a spring-mass-damper model.

Furthermore, it can also be considered that the differential equation exemplified in Equation 3 represents a movement of an object m in a spring-mass-damper model exemplified in FIG. 5. FIG. 5 is a diagram conceptually representing one example of a spring-mass-damper model.

A spring-mass-damper model includes a damper part c representing resistance force against the object m, a spring part k which produces a movement in which the object m vibrates, and an external force part representing the force F externally applied to the object m. For example, the object m moves upward as the external force F is upwardly applied to the object m represented by the spring-mass-damper model. When the object m moves upward, length of the spring part k becomes shorter than equilibrium length. As a result, downward force is exerted on the object m by the spring part k. Further, resistance force in a direction opposite to a direction in which the object m moves is generated in the object m by the damper part c. The object m soon starts moving downward by downward force applied thereto by the spring part k. As the object m moves downward, the length of the spring part k becomes longer than the equilibrium length. In this case, the spring part k applies upward force to the object m. The object m soon starts moving upward by the upward force. Unless the force F is continuously applied to the object m, the object m longitudinally vibrates by the spring part k. However, resistance force is applied in a direction opposite to a direction in which the object m moves is applied to the object m by the damper part c. Therefore, the object m longitudinally vibrates while decreasing width of longitudinal vibration.

By discretizing the differential equation exemplified in Equation 3 in relation to time, information (exemplified in Equation 1) representing a relevance of blood-vessel internal pressure (one example of a state) at a plurality of timings is acquired. Discretization is performed, for example, by dividing time at each time. The processing g exemplified in Equation 1 represents processing of acquiring, in accordance with the relevance, blood-vessel internal pressure (one example of a state) at a second timing from blood-vessel internal pressure (one example of a state) at a first timing. For example, the information conceptually represents processing of solving the differential equation exemplified in Equation 3 in accordance with a processing procedure such as an explicit method, an implicit method, or the like. In this case, the parameters θ in Equation 1 are the volume of blood flow m, the blood resistance k, and the blood viscosity c in Equation 3.

Figure 2:
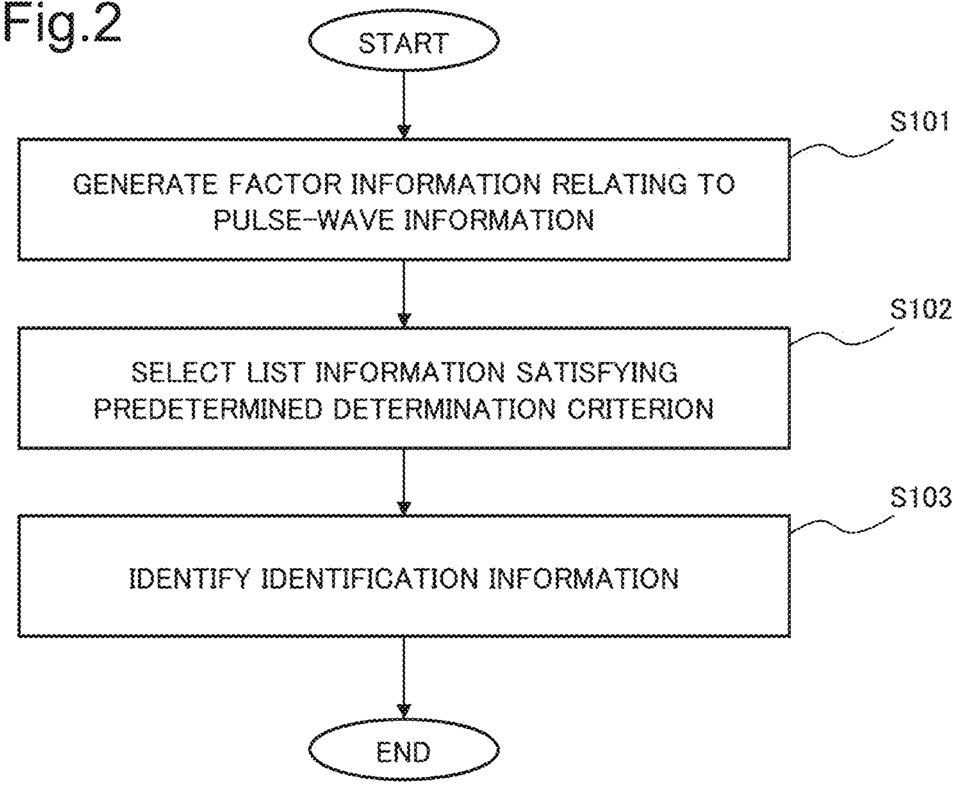
FIG. 2 is a flowchart illustrating flow of processing in the identification device according to the first example embodiment.

Furthermore, processing h exemplified in FIG. 2 is information representing a relevance between a solution (e.g., blood-vessel internal pressure at the timing t) of the differential equation (Equation 3), and measurement information (e.g., a size of a pulse wave).

In step S101 illustrated in FIG. 2, the generation unit 102 calculates a value of the parameter θ in accordance with a scheme such as data assimilation processing, along with model estimation processing acquired in relation to each timing, for example, in such a way as to decrease an error between information ($y_t$) generated in accordance with the processing indicated in Equations 1 and 2, and actually measured measurement information. Factor information is, for example, at least one parameter among parameters calculated in accordance with the model estimation processing. Alternatively, the generation unit 102 may estimate a value of the parameter θ in accordance with a scheme such as a least-squares method. Therefore, it can also be said that processing in which the generation unit 102 estimates a value of the parameter θ is processing of generating factor information relating to a pulse wave represented by pulse-wave information. Factor information in the list information illustrated in FIG. 4 is generated, for example, by continuously connecting, in relation to one of the parameters θ, values each calculated at each timing.

Figure 6:
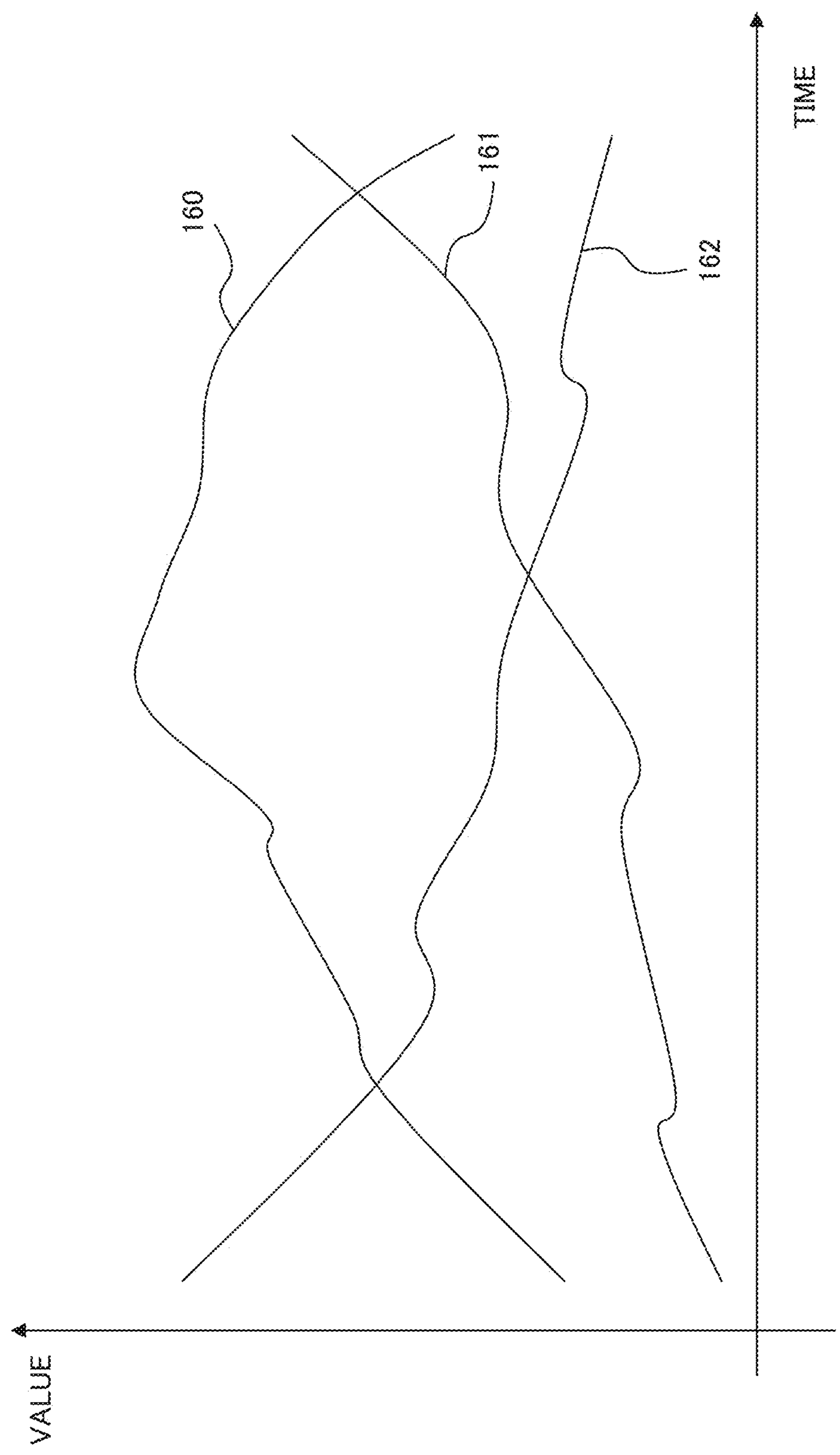
FIG. 6 is a diagram conceptually representing one example of factor information.

In accordance with the processing as described above, the generation unit 102 generates, for example, factor information exemplified in FIG. 6. FIG. 6 is a diagram conceptually representing one example of factor information. A horizontal axis in FIG. 6 represents time, and represents that time elapses toward a right side. A vertical axis in FIG. 6 represents a value represented by factor information, and represents that a value of factor information is greater on an upper side.

FIG. 6 exemplifies, as factor information, blood flow volume information (a curve 162) representing a volume of blood flow, blood vessel resistance information (a curve 160) representing blood vessel resistance, and blood viscosity information (a curve 161) representing blood viscosity. The blood flow volume information, the blood vessel resistance information, and the blood viscosity information are information representing magnitude of the parameter θ calculated, based on pulse-wave information, and in accordance with the processing indicated in Equations 1 and 2. When pulse wave represented by pulse-wave information (exemplified in FIG. 3) changes as time elapses, a value of factor information (exemplified in FIG. 6) also changes.

Furthermore, model information representing blood-vessel internal pressure is not limited to the differential equation exemplified in Equation 3. For example, when a plurality of reflected waves according to an ejection wave are measured in pulse-wave information (exemplified in FIG. 3), model information may be a differential equation representing a model in which the spring-mass-damper models exemplified in FIG. 5 are connected in series.

Next, a predetermined determination criterion is described. A predetermined determination criterion has only to be a determination criterion relating to factor information (exemplified in FIG. 6) generated in relation to at least one or more timings. A predetermined determination criterion is information representing a determination criterion for determining whether two pieces of information are similar (or coincident). For example, the predetermined determination criterion is a criterion that a similarity degree relating to the two pieces of information is greater than a predetermined threshold (however, a threshold value is a positive value). It is assumed that, as a degree at which two pieces of information are similar is greater, the similarity degree is greater. Moreover, it is assumed that, as a degree at which two pieces of information are similar is smaller, the similarity degree becomes closer to 0. Since various methods are known as methods of calculating a similarity degree between pieces of information, description relating to a method of calculating a similarity degree is omitted.

A predetermined determination criterion may be, for example, a criterion based on a distance between two pieces of information. It is assumed that, as a degree at which two pieces of information are similar is greater, the distance becomes closer to 0. It is assumed that, as a degree at which two pieces of information are similar is smaller, the distance is greater. In this case, a predetermined determination criterion is, for example, a criterion that a distance relating to two pieces of environment information is smaller than a threshold value. A predetermined determination criterion is not limited to the example described above.

Biological-model information (exemplified in Equations 1 and 2) is not limited to the example described above, and may be, for example, a predetermined function such as a polynomial equation, an exponential function, or a logarithmic function.

Next, an effect relating to the identification device 101 according to the first example embodiment of the present invention is described.

The identification device 101 according to the first example embodiment can correctly identify an identification target. A reason for this is that the identification device 101 analyzes, based on biological-model information, a factor that a pulse wave is generated.

Furthermore, as described later in the fourth example embodiment, an identification target can be more correctly identified by using a pulse wave measured in a period in which pressure controlled in accordance with a predetermined pressure control procedure is applied. A reason for this is that elasticity of blood vessels and a blood vessel diameter differ from biological subject to biological subject, and a pulse wave including an influence of the elasticity, the blood vessel diameter, or the like is measured by using the pulse wave of an identification target (biological subject) in a period in which pressure is applied. Moreover, the identification device 101 according to the first example embodiment identifies a biological subject, based on more pieces of information relating to the biological subject, and therefore, can build a more robust authentication system. Note that, in a case of pressure controlled in accordance with a predetermined pressure control procedure, pulse-wave information itself may be used as factor information, as described later in the fourth example embodiment.

Second Example Embodiment

Next, a second example embodiment of the present invention based on the above-described first example embodiment is described.

Figure 7:
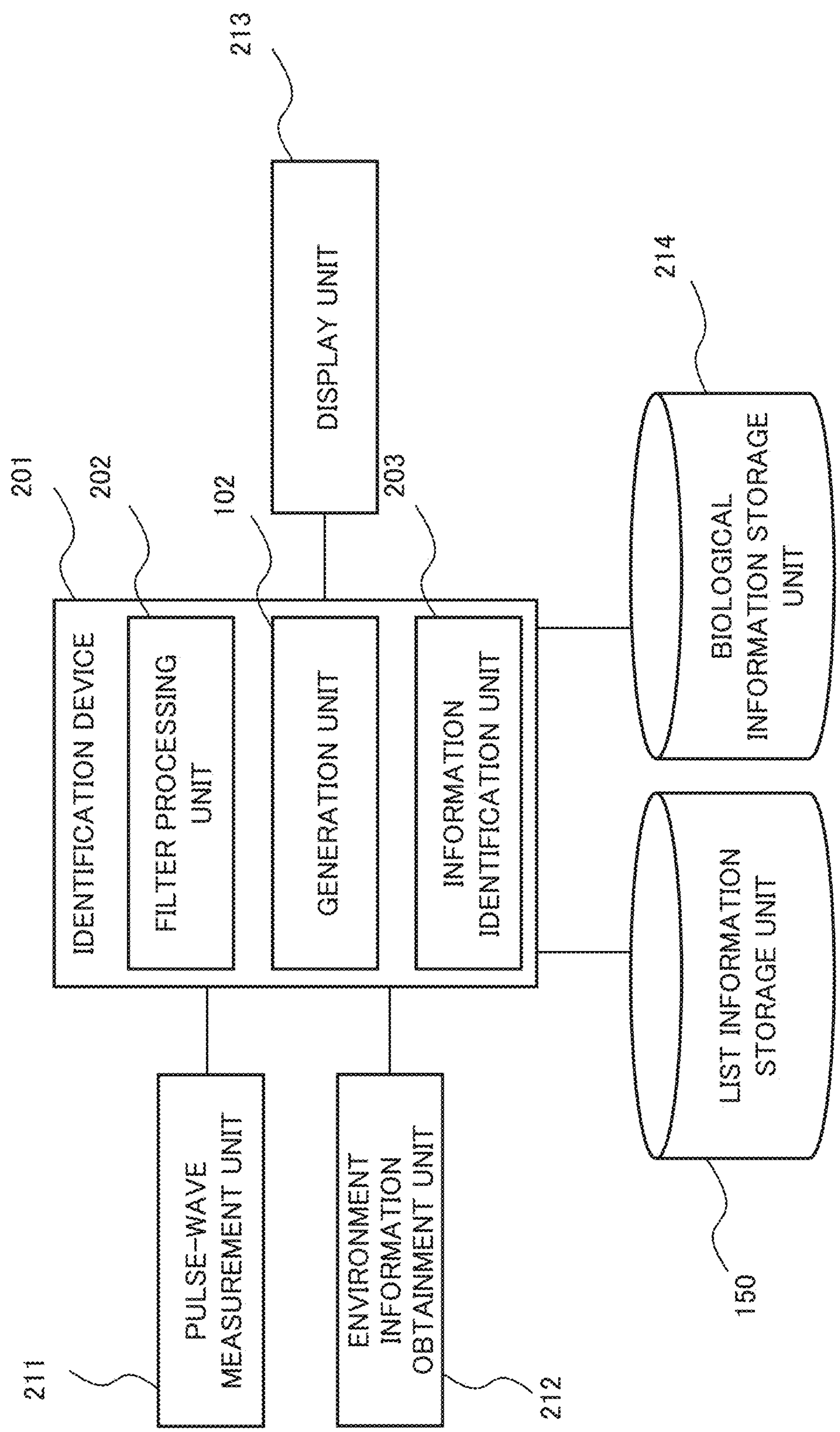
FIG. 7 is a block diagram illustrating a configuration included in an identification device according to a second example embodiment of the present invention.

A configuration included in an identification device 201 according to the second example embodiment of the present invention is described in detail with reference to FIG. 7. FIG. 7 is a block diagram illustrating a configuration included in the identification device 201 according to the second example embodiment of the present invention.

The identification device 201 according to the second example embodiment includes a generation unit 102, an information identification unit 203, and a filter processing unit 202.

The identification device 201 may be connected to a display unit 213. The identification device 201 is communicably connected to a pulse-wave measurement unit 211, an environment information obtainment unit 212, a list information storage unit 150, and a biological information storage unit 214. Alternatively, the identification device 201 may include the pulse-wave measurement unit 211, the environment information obtainment unit 212, the list information storage unit 150, and the biological information storage unit 214.

The pulse-wave measurement unit 211 measures a pulse wave of a biological subject (or an identification target), and generates pulse-wave information representing the measured pulse wave. The pulse-wave measurement unit 211 is achieved by use of, for example, an acceleration sensor, a pressure sensor, a photoelectric sensor, an optical sensor, a red-green-blue (RGB) camera, or the like.

The list information storage unit 150 stores list information as described above with reference to FIG. 4.

The biological information storage unit 214 stores, for example, biological information exemplified in FIG. 9. FIG. 9 is a diagram conceptually representing one example of biological information.

Biological information represents information relating to a pulse wave of a biological subject. In the biological information exemplified in FIG. 9, identification information representing an identifier, a measurement date and time, water information, pressure information representing presence or absence of pressure, a heart rate, highest blood pressure, lowest blood pressure, dosing information, and the like are associated with one another. Identification information is information representing an identifier being capable of identifying the biological subject. A measurement date and time is a date and time when a pulse wave of the biological subject is measured. Water information is information representing a volume of water taken by a biological subject before a measurement timing when pulse-wave information is measured, and within a predetermined time from the measurement timing. Pressure information is information representing whether the biological subject is pressured in accordance with a predetermined pressure control procedure, in a period in which a pulse wave of the biological subject is measured. A heart rate is a heart rate of the biological subject near the measurement timing. Highest blood pressure is highest blood pressure of the biological subject near the measurement timing. Lowest blood pressure is lowest blood pressure of the biological subject near the measurement timing. Dosing information is information representing a kind of medicine taken by a biological subject before a measurement timing when pulse-wave information is measured, and within a predetermined time from the measurement timing. Therefore, biological information is information including information representing a factor influencing a pulse wave of the biological subject.

The biological information exemplified in FIG. 9 includes biological information associating information indicated by information 1 to 8 below.

(Information 1) identification information "B", (Information 2) measurement date and time "2017/3/3 10:12", (Information 3) water information "100", (Information 4) pressure information "none", (Information 5) heart rate "63", (Information 6) highest blood pressure "120", (Information 7) lowest blood pressure "70", and (Information 8) dosing information "MB".

The biological information represents that, in relation to a biological subject represented by the identification information "B", a pulse wave is measured in a period in which the biological subject is not pressured on the measurement date and time "2017/3/3 10:12". Moreover, the biological information represents that, when a pulse wave is measured, the biological subject takes the water indicated by "100", and further takes a medicine represented by "MB". Further, the biological information represents that, when the pulse wave is measured, the heart rate of the biological subject is "63", the highest blood pressure of the biological subject is "120", and the lowest blood pressure of the biological subject is "70".

The biological information may include information (e.g., height, weight, a medical history, or genes) different from the information 1 to 8 described above. The biological information may include, for example, medical record information describing a diagnosis by a doctor relating to the biological subject, or medical history information representing a history of a disease suffered by the biological subject. Additionally, the biological information does not necessarily need to include all the information exemplified in the information 1 to 8. The biological information is not limited to the example described above.

The pulse-wave measurement unit 211 measures a pulse wave of an identification target (or a biological subject), and generates pulse-wave information representing the measured pulse wave. The pulse-wave measurement unit 211 inputs the generated pulse-wave information to the filter processing unit 202.

Furthermore, in a period in which the pulse-wave measurement unit 211 measures a pulse wave of the identification target, the environment information obtainment unit 212 measures a state relating to the identification target, or an environment around the identification target. The environment information obtainment unit 212 is achieved by, for example, an acceleration sensor attached to the identification target, a sound collecting device placed around the identification (or in the identification target), an image capturing device capturing the biological subject, an air pressure sensor (or a thermometer) placed around the identification target, or the like. The environment information obtainment unit 212 may be a gyrosensor attached to an identification target. For example, when achieved by a sound collecting device, the environment information obtainment unit 212 collects voice, sound, and the like around an identification target that is measured a pulse wave. For example, when achieved by an acceleration sensor, the environment information obtainment unit 212 measures acceleration generated in the identification target according to a movement of the identification target. For example, when achieved by an air pressure sensor, the environment information obtainment unit 212 measures pressure around the identification target.

Environment information is information having a possibility of affecting a pulse wave of an identification target (or a biological subject). For example, a pulse wave measured in a period in which an identification target is moving, and a pulse wave measured in a period in which an identification target is motionless are not necessarily pulse waves having the same waveform. Moreover, a pulse wave measured in a period in which an identification target stays together with a particular person (e.g., a doctor), and a pulse wave measured in a period in which the identification target is alone are not necessarily pulse waves having the same waveform.

The environment information obtainment unit 212 generates environment information representing acquired information, and inputs the generated environment information to the information identification unit 203. Moreover, the environment information obtainment unit 212 may execute processing of removing an influence by the environment information from the pulse-wave information generated by the pulse-wave measurement unit 211.

Figure 8:
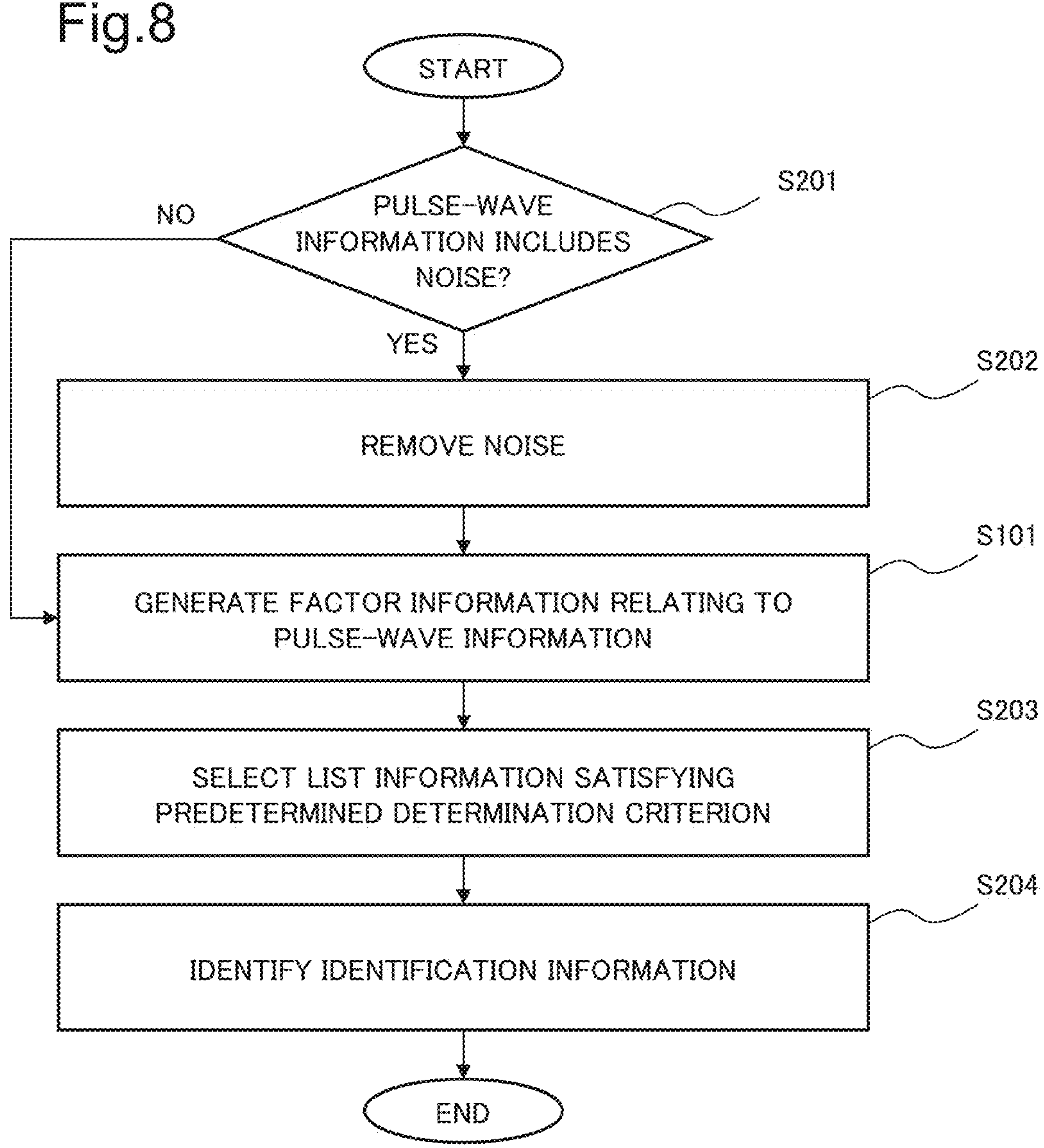
FIG. 8 is a flowchart illustrating flow of processing in the identification device according to the second example embodiment.

Processing in the identification device 201 according to the second example embodiment of the present invention is described in detail with reference to FIG. 8. FIG. 8 is a flowchart illustrating flow of processing in the identification device 201 according to the second example embodiment.

The filter processing unit 202 receives pulse-wave information representing a pulse wave of an identification target. The filter processing unit 202 determines whether the pulse-wave information includes information representing noise (e.g., an irregular pulse of the biological subject) (step S201). When the filter processing unit 202 determines that the pulse-wave information does not include noise (NO in step S201), processing indicated in step S202 is not executed. In this case, the filter processing unit 202 inputs the pulse-wave information to the generation unit 102. When the filter processing unit 202 determines that the pulse-wave information includes noise (YES in step S201), the filter processing unit 202 removes the noise from the pulse-wave information (step S202). The filter processing unit 202 may further store, in the biological information storage unit 214, information associating information representing the noise with identification information representing an identifier relating to an identification target from which noise is detected. Alternatively, the filter processing unit 202 may display, on the display unit 213, information representing that noise is detected.

The generation unit 102 receives the pulse-wave information, and generates factor information (exemplified in FIG. 6) relating to the pulse-wave information by executing processing similar to processing described with reference to FIG. 2 (step S101).

The information identification unit 203 receives the factor information (exemplified in FIG. 6) generated by the generation unit 102. The information identification unit 203 acquires at least either environment information generated by the environment information obtainment unit 212 or biological information stored in the biological information storage unit 214.

Processing executed in the identification device 201 according to the present example embodiment is described with reference to an example in which the information identification unit 203 acquires the environment information. It is assumed that identification information relating to an identifier representing a biological subject, factor information generated based on pulse wave information relating to the biological subject, and environment information when the pulse wave information is measured are associated with one another in the list information storage unit 150. In the list information storage unit 150, biological information relating to the biological subject may be further associated with the identification information.

The information identification unit 203 selects, out of list information stored in the list information storage unit 150, list information satisfying a predetermined determination criterion in relation to the received factor information and the received environment information (step S203).

In the processing indicated in step S203, the information identification unit 203 selects, for example, list information including environment information in which the received environment information, and environment information in the list information satisfy a predetermined determination criterion. The information identification unit 203 further selects list information (hereinafter, represented as "identification list information") in which received environment information, and factor information in the selected list information satisfy a predetermined determination criterion (step S203). The information identification unit 203 identifies identification information representing an identifier included in the identification list information (step S204).

Even when identifying identification list information, based on biological information, or the biological information and the environment information, the information identification unit 203 executes processing similar to the processing described above in relation to environment information. The information identification unit 203 selects, for example, list information including biological information in which received biological information, and biological information in the list information satisfy a predetermined determination criterion, and further selects identification list information in the selected list information.

Next, an effect relating to the identification device 201 according to the second example embodiment of the present invention is described.

The identification device 201 according to the second example embodiment can correctly identify a biological subject. A reason for this is similar to the reason described in the first example embodiment.

Furthermore, the identification device 201 according to the second example embodiment can more accurately identify an individual. A reason for this is that, even in a situation where a pulse wave of a biological subject varies according to a state of the biological subject, an environment around the biological subject, and the like, the biological subject is identified based on data according to the situation or the environment.

In the example described above, the information identification unit 203 identifies an individual, based on environment information generated by the environment information obtainment unit 212. When a degree at which a pulse wave changes according to environment information (a degree at which a volume of blood flow increases (or a degree at which a pulse wave changes) when a user is moving, or the like) is previously known, the information identification unit 203 may adjust, based on the environment information, a pulse wave measured by the pulse-wave measurement unit 211. Similarly, when a degree at which a volume of blood flow increases according to measurement information (e.g., a degree at which a volume of blood flow increases (or a degree at which a pulse wave changes) when air pressure changes, or the like) is previously known, the information identification unit 203 may adjust, based on the environment information, a pulse wave measured by the pulse-wave measurement unit 211.

Third Example Embodiment

Next, a third example embodiment of the present invention is described.

Figure 10:
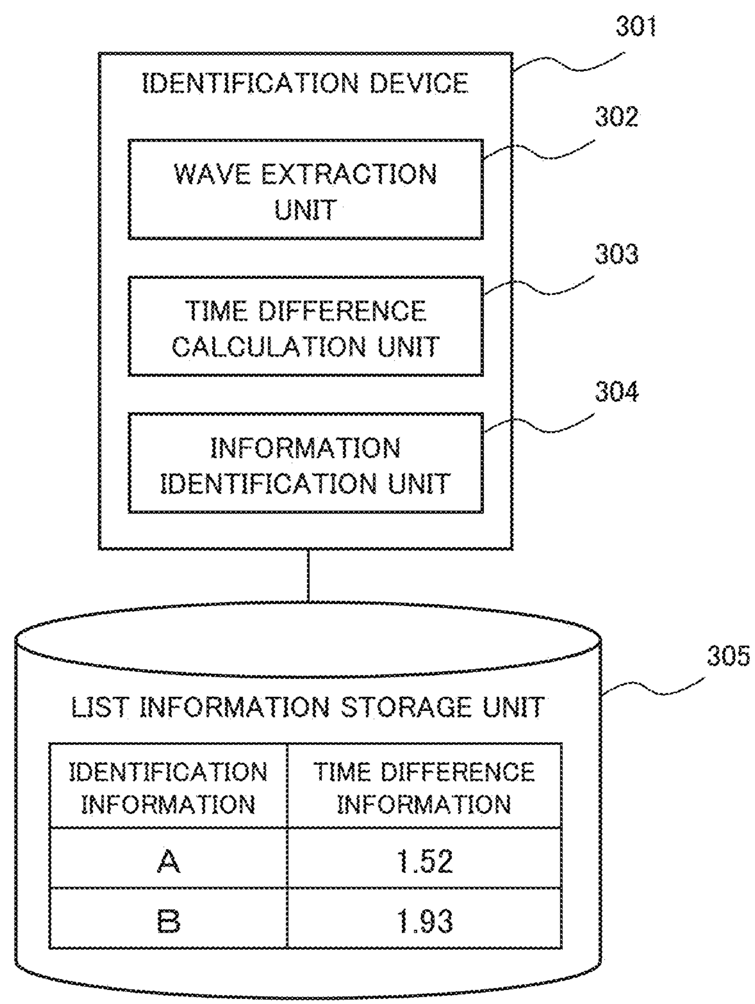
FIG. 10 is a block diagram illustrating a configuration included in an identification device according to a third example embodiment of the present invention.

A configuration included in an identification device 301 according to the third example embodiment of the present invention is described in detail with reference to FIG. 10. FIG. 10 is a block diagram illustrating a configuration included in the identification device 301 according to the third example embodiment of the present invention.

The identification device 301 according to the third example embodiment includes a wave extraction unit 302, a time difference calculation unit 303, and an information identification unit 304.

The identification device 301 is communicably connected to a list information storage unit 305. The identification device 301 may include the list information storage unit 305.

Figure 12:
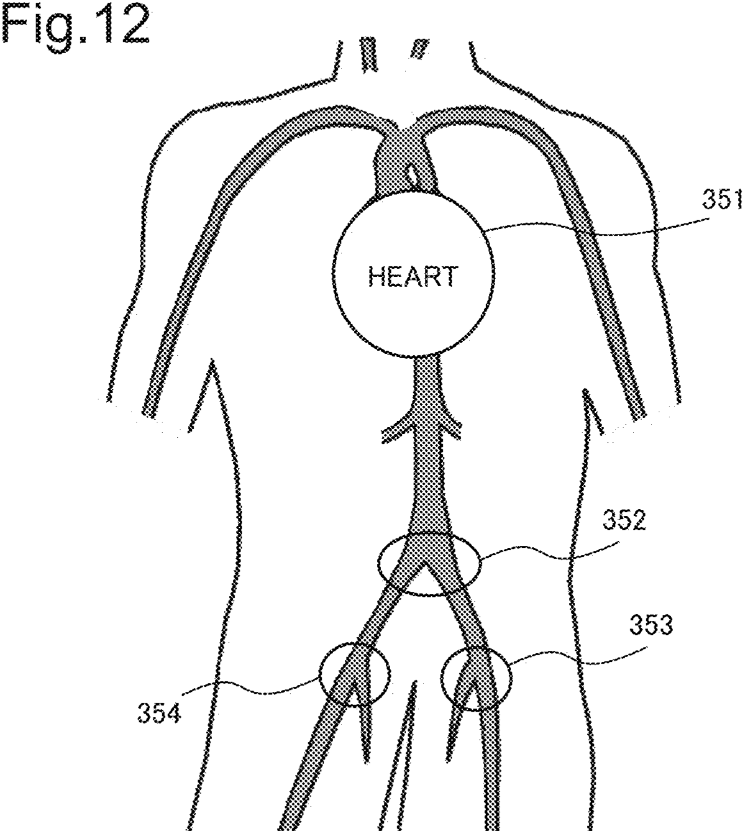
FIG. 12 is a schematic diagram conceptually illustrating blood vessels, a heart, and the like in a biological subject.

The list information storage unit 305 stores list information associating identification information relating to an identifier representing a biological subject, with time difference information representing a time difference among a plurality of waves included in a pulse wave measured in the biological subject. Waves included in the pulse wave are, for example, an ejection wave, and a reflected wave according to the ejection wave. An ejection wave and a reflected wave are described with reference to FIG. 12. FIG. 12 is a schematic diagram conceptually illustrating blood vessels, a heart, and the like in a biological subject.

A heart 351 of a biological subject is beating. Blood in the heart 351 is caused to flow out into an artery connected to the heart 351, according to beating of the heart 351. The artery is connected to each organ in the biological subject while repeating bifurcation (a bifurcation 352, a bifurcation 353, a bifurcation 354, and the like). Blood being caused to flow out from the heart 351 soon reaches each organ while passing through the artery. Blood collides with a blood vessel wall when passing through a bifurcation (hereinafter, represented as a "blood vessel bifurcation") or the like in the artery, and thereby, disturbs flow of blood. Blood-vessel internal pressure changes according to an outflow of blood from the heart 351 or collision of blood with a blood vessel wall (or a bifurcation).

Figure 13:
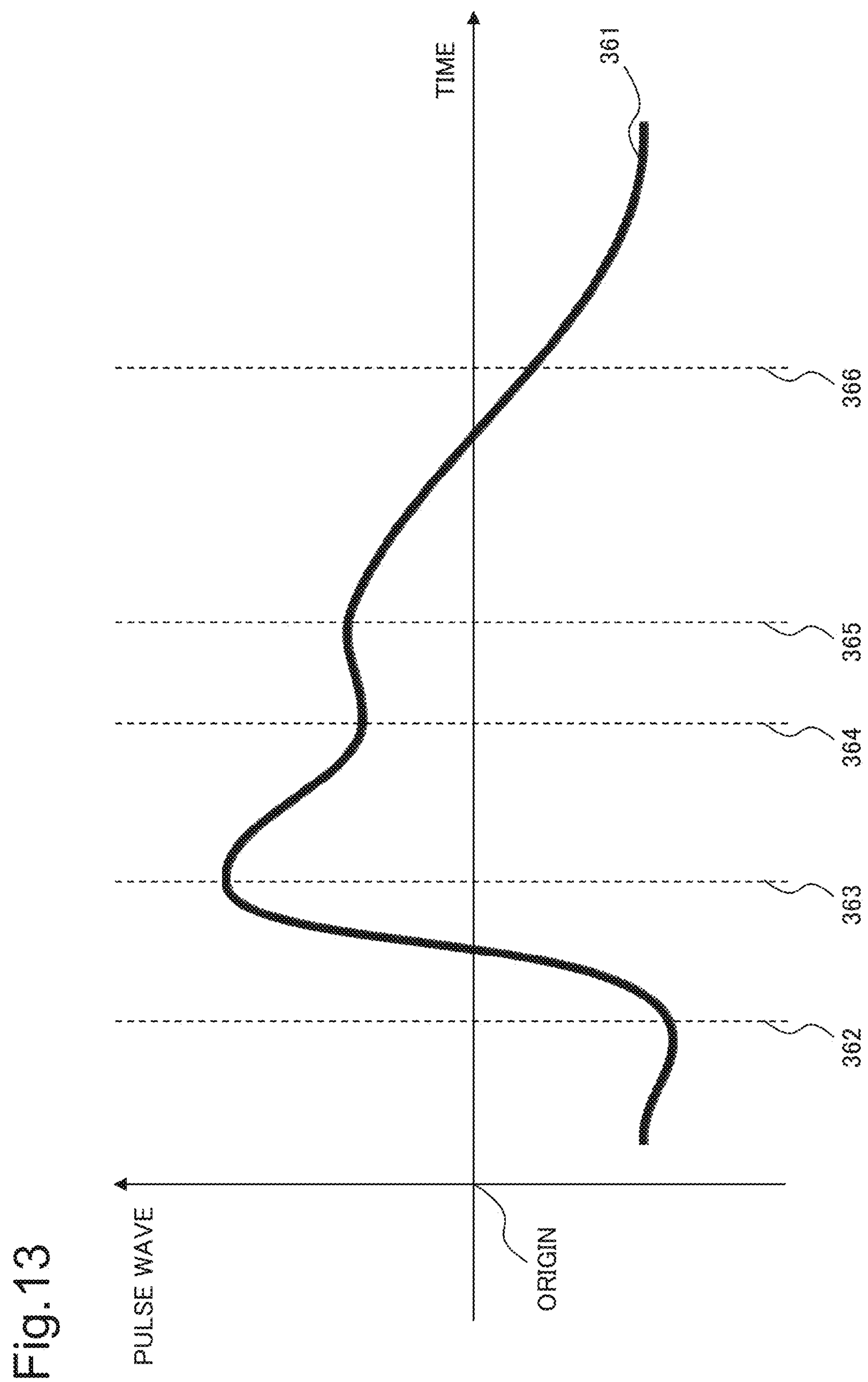
FIG. 13 is a diagram conceptually representing one example of a pulse wave of a biological subject (or an identification target).

A blood vessel wall is usually soft. Therefore, a blood vessel (in this case, artery) wall is deformed according to change in blood-vessel internal pressure. Pulse-wave information (exemplified in FIG. 3) is generated, for example, by measuring vibration of a skin surface generated according to deformation of a blood vessel wall in a biological subject. A pulse wave is described with reference to FIG. 13. FIG. 13 is a diagram conceptually representing one example of a pulse wave of a biological subject (or an identification target). A horizontal axis in FIG. 13 represents time, and represents that time elapses toward a right side. A vertical axis in FIG. 13 represents a size of a pulse wave, and represents that the size is larger at a greater distance from an origin. A curve 361 conceptually represents a pulse wave measured by one outflow of blood by the heart 351.

A wave in a period from a timing 362 to a timing 364 is a wave on which vibration formed by blood being caused to flow out from the heart 351 is measured. The wave in a period from the timing 362 to the timing 364 is called an "ejection wave". A wave in a period from the timing 364 to a timing 366 is, for example, a wave on which change in blood-vessel internal pressure caused by disturbance of blood flow at a blood vessel bifurcation is measured. The wave in a period from the timing 364 to the timing 366 is called a "reflected wave".

A blood vessel bifurcation exists in, for example, an aorta abdominalis, a common iliac artery, or the like. Change in blood-vessel internal pressure caused at a blood vessel bifurcation reaches a measurement part as a wave via blood, and the wave that has reached is measured as a reflected wave. Therefore, a timing at which an ejection wave is generated (or a timing 363 at which amplitude of an ejection wave becomes maximum, or the like) is different from a timing at which a reflected wave generated according to the ejection wave is generated (or a timing 365 at which amplitude of the reflected wave becomes maximum, or the like). Moreover, in a pulse wave, one reflected wave is not necessarily generated according to an ejection wave, and a plurality of reflected waves may be generated according to an ejection wave. Therefore, a time difference between an ejection wave and a reflected wave is determined according to, for example, hardness of blood vessels in a biological subject, a distance from the heart 351 to a blood vessel bifurcation, a distance between a plurality of blood vessel bifurcations, and the like. Hardness of blood vessels, and these distances generally differ among different biological subjects. Therefore, a pulse wave to be measured also differs from biological subject to biological subject.

Figure 11:
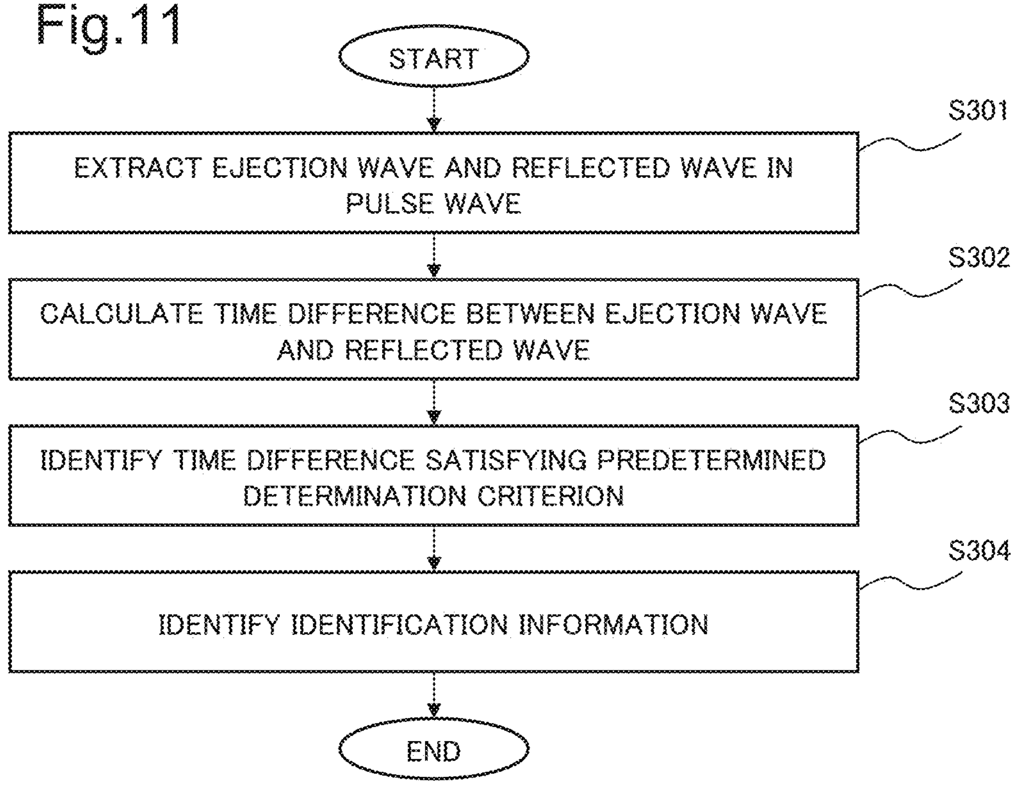
FIG. 11 is a flowchart illustrating flow of processing in the identification device according to the third example embodiment.

Next, processing in the identification device 301 according to the third example embodiment of the present invention is described in detail with reference to FIG. 11. FIG. 11 is a flowchart illustrating flow of processing in the identification device 301 according to the third example embodiment.

The wave extraction unit 302 receives pulse-wave information (exemplified in FIG. 13) representing a pulse wave of an identification target. For convenience of description, it is assumed that pulse-wave information is a pulse wave measured by one outflow of blood by the heart 351. In other words, it is assumed that pulse-wave information includes one ejection wave and one or more reflected waves. When pulse-wave information represents a pulse wave measured by a plurality of outflows of blood by the heart 351, the wave extraction unit 302 executes, for a pulse wave measured for each outflow, processing described later with reference to steps S301 to S304.

Pulse-wave information may be represented, for example, by use of a predetermined function (e.g., Fourier series), or by temporal change in a size of a pulse wave. Moreover, pulse-wave information may be represented by a characteristic value representing a characteristic of a pulse wave. A characteristic value is, for example, a timing at which an inflection point is generated, a size of a pulse wave at the timing, a timing at which change of a pulse wave is minimum (or maximum), or the like. Pulse-wave information is not limited to the example described above.

In a pulse wave represented by the received pulse-wave information (exemplified in FIG. 13), the wave extraction unit 302 extracts an ejection wave and a reflected wave (step S301). The wave extraction unit 302 specifies, for example, a plurality of timings at which a pulse wave represented by pulse-wave information starts decreasing (i.e., a pulse wave is maximum). The wave extraction unit 302 specifies a size of amplitude at each timing, and extracts, as an ejection wave, a wave at the timing 363 at which a specified size is largest and appears for the first time. Among specified timings, the wave extraction unit 302 extracts, as a reflected wave, a wave at the timing 365 differing from the timing 363 at which the wave extraction unit 302 extracts as an ejection wave.

The wave extraction unit 302 may specify the plurality of timings, for example, by acquiring timings (the timing 362, the timing 364, and the like) at which a pulse wave represented by pulse-wave information (exemplified in FIG. 13) starts increasing. Alternatively, the wave extraction unit 302 may specify the plurality of timings by acquiring an inflection point of a pulse wave. Processing of extracting a plurality of timings is not limited to the example described above.

Hereinafter, for convenience of description, it is assumed that the wave extraction unit 302 extracts an ejection wave and one reflected wave in a pulse wave represented by pulse-wave information.

The time difference calculation unit 303 calculates a time difference between the extracted ejection wave and the reflected wave (step S302), and generates time difference information representing the calculated time difference. The time difference calculation unit 303 calculates the time difference, for example, by calculating a difference of timings (e.g., the timing 363 and the timing 365 in FIG. 13) at which the wave extraction unit 302 extracts. Alternatively, the time difference calculation unit 303 may calculate the difference, based on a characteristic value representing a characteristic of a wave. The characteristic value is, for example, a timing at which a wave becomes maximum, a timing at which the wave starts increasing, a timing at an inflection point of the wave, or the like. The characteristic value is not limited to the example described above.

The information identification unit 304 specifies a time difference in which a time difference in list information (exemplified in FIG. 10) and a time difference calculated by the time difference calculation unit 303 satisfy a predetermined determination criterion (step S303). The information identification unit 304 identifies identification information representing an identifier in list information including the identified time difference (step S304). A predetermined determination criterion is, for example, a determination criterion that a difference between the two time differences is smaller than a predetermined threshold value. A predetermined determination criterion may be, for example, a criterion that a ratio between the two time differences is within a predetermined range (e.g., a range from 0.95 to 1.05). A predetermined determination criterion is not limited to the example described above, and has only to be a criterion representing that the two time differences are the same (or similar).

For example, when a time difference calculated by the time difference calculation unit 303 is "1.52", the information identification unit 304 specifies a time difference "1.52" (a first row in the list information in FIG. 10) in which a time difference in list information (exemplified in FIG. 10) and the calculated time difference "1.52" satisfy a predetermined determination criterion. The information identification unit 304 identifies identification information "A" associated with the specified time difference "1.52".

Next, an effect relating to the identification device 301 according to the third example embodiment of the present invention is described.

The identification device 301 according to the third example embodiment can correctly identify a biological subject. A reason for this is that a time difference between an ejection wave and a reflected wave according to the ejection wave is determined according to length from the heart 351 to a blood vessel bifurcation, or the like, and the identification device 301 identifies an identification target, based on the time difference. Length from the heart 351 to a blood vessel bifurcation generally is different for each biological subject, and is information difficult to disguise. The identification device 301 identifies a biological subject, based on information difficult to disguise, and therefore, can provide information being a basis for building an authentication system having a strong resistance to impersonation.

The identification device 301 identifies an identification target, based on a time difference between an ejection wave and a reflected wave in the example described above, but may identify an identification target, based on a time difference among a plurality of reflected waves. For example, when a pulse wave includes a plurality of reflected waves, the identification device 301 may identify a reflected wave according to a size order of amplitude. For example, when a pulse wave represented by pulse-wave information includes first to fifth reflected waves, the identification device 301 identifies an identification target by executing processing similar to the processing described with reference to FIG. 11, based on, for example, a time difference between the second reflected wave and the third reflected wave. As descried above in relation to a relation between an ejection wave and a reflected wave, a time difference among a plurality of reflected waves is determined by, for example, a distance between a plurality of blood vessel bifurcations, or the like. Since these distances are information difficult to disguise, the identification device 301 can provide information being a basis for building an authentication system having a strong resistance to impersonation.

Furthermore, the identification device 301 can provide information being a basis for building an authentication system having a stronger resistance to impersonation, by identifying a biological subject, based on a plurality of time differences (e.g., a time difference between an ejection wave and a reflected wave, a time difference between the first reflected wave and the second reflected wave, and the like).

Fourth Example Embodiment

Next, a fourth example embodiment of the present invention based on each of the above-described example embodiments is described.

A configuration included in an identification device 401 according to the fourth example embodiment of the present invention is described in detail with reference to FIG. 14. FIG. 14 is a block diagram illustrating a configuration included in the identification device 401 according to the fourth example embodiment of the present invention.

The identification device 401 according to the fourth example embodiment includes a pulse-wave measurement unit 410, a cuff 411, and an information identification unit 403. The identification device 401 may include a generation unit 402.

The identification device 401 is communicably connected to a list information storage unit 412. The identification device 401 may include the list information storage unit 412.

A control unit 404 controls the pulse-wave measurement unit 410 and a pump 405.

The cuff 411 can store therein gas such as air, or liquid such as water. The cuff 411 is connected to the pump 405. The cuff 411 is attached to at least some parts of a biological subject. The pump 405 injects gas (or liquid) into the cuff 411, or discharges, from the cuff 411, gas (or liquid) stored in the cuff 411. The control unit 404 controls an operation of the pump 405 in accordance with a predetermined pressure control procedure.

The predetermined pressure control procedure is, for example, a procedure of controlling the pump 405 in such a way as to inject gas (or liquid) into the cuff 411 until internal pressure of the cuff 411 reaches to predetermined pressure, and controlling the pump 405 in such a way as to gradually discharge gas (or liquid) stored in the cuff 411 when the internal pressure becomes equal to or more than predetermined pressure. The predetermined pressure control procedure may be, for example, such a control procedure as to control internal pressure of the cuff 411 within a range of pressure (i.e., pressure being equal to or less than highest blood pressure of a biological subject) at which a pulse wave can be detected. The predetermined pressure control procedure may be, for example, a procedure of controlling the pump 405 in such a way as to periodically (or aperiodically) change internal pressure of the cuff 411 within the pressure range. The predetermined pressure control procedure may be, for example, a procedure of controlling the pump 405 in such a way as to periodically (or aperiodically) change internal pressure of the cuff 411 within a predetermined pressure range. Moreover, the predetermined pressure range may include pressure being equal to or more than highest blood pressure of a biological subject, or may include pressure within a range that does not pressure a biological subject. The predetermined pressure control procedure may be a procedure of controlling the pump 405 in such a way as to apply constant pressure. In other words, the predetermined pressure control procedure is not limited to the example described above.

Furthermore, a pulse wave measured in a period in which a part of a biological subject is pressured by the cuff 411 changes according to magnitude of the pressure. For example, a pulse wave (exemplified in (A) of FIG. 3) measured in a period in which the pressure is applied is different from a pulse wave (exemplified in (B) of FIG. 3) measured in a period in which the pressure is not applied.

The pulse wave exemplified in (A) of FIG. 3 is a pulse wave measured by the pulse-wave measurement unit 410 in a period in which the pump 405 is controlled in such a way that internal pressure of the cuff 411 increases gradually in a predetermined pressure control procedure. Referring to a pulse wave, amplitude of the pulse wave increases as time elapses. This represents that external pressure is applied to blood vessels as pressure applied to a part by the cuff 411 becomes high, and blood-vessel internal pressure becomes high as the external pressure is applied. Referring to the pulse wave exemplified in (B) of FIG. 3, it is seen that amplitude of the pulse wave is constant (or substantially constant). This represents that external pressure is not applied to blood vessels.

Furthermore, referring to the pulse wave exemplified in (A) of FIG. 3, a waveform of the pulse wave changes as external pressure is applied to blood vessels (i.e., as time elapses). When a first wave (from a timing 31 to a timing 33) in the pulse wave is compared with a second wave (from a timing 33 to a timing 37), a size of the pulse wave decreases in a period from the timing 32 to the timing 33 in the first wave, whereas the second wave includes a period (a period from the timing 35 to the timing 36) in which a size of the pulse wave increases in a period from the timing 34 to the timing 37. These periods both represent a period from a point after a heart causes blood to flow out into blood vessels, to a point until blood is caused to flow out next. Therefore, it is considered that a difference of waveforms between the first wave and the second wave is, for example, a difference produced according to hardness of blood vessels, or the like.

In contrast, referring to the pulse wave exemplified in (B) of FIG. 3, a waveform of the pulse wave hardly changes in both a first wave (from a timing 41 to a timing 42) and a second wave (from a timing 42 to a timing 43). This represents that a pulse wave is measured with a constant (or substantially constant) waveform in a period in which external pressure is not applied to blood vessels.

Furthermore, the list information storage unit 412 stores list information associating identification information representing an identifier for identifying an individual (or an identification target), with information relating to a pulse wave measured in relation to the individual. The information relating to the pulse wave is information relating to a pulse wave measured by the pulse-wave measurement unit 410 in a period in which internal pressure of the cuff 411 is controlled in accordance with a predetermined pressure control procedure. For convenience of description, it is assumed that pulse-wave information in the list information is information relating to a pulse wave previously measured before processing as described later with reference to FIG. 15. However, when an individual is not identified based on information relating to a pulse wave, list information associating identification information representing an identifier relating to an individual with information relating to the pulse wave may be stored in the list information storage unit 412. Moreover, information relating to a pulse wave may be factor information as described above in the first example embodiment, may be a time difference between an ejection wave and a reflected wave as described above in the third example embodiment, or may be information including environment information, biological information, or the like. List information is not limited to the example described above.

In addition, the identification device 401 may include a blood pressure measurement unit (not illustrated) which measures blood pressure (highest blood pressure and lowest blood pressure) of a user. In this case, the identification device 401 can measure blood pressure of the user in single processing, and further identify the user.

The generation unit 402 is achieved by the generation unit 102 (FIG. 1) according to the first example embodiment, the generation unit 102 (FIG. 7) according to the second example embodiment, or functions similar to the functions included in the wave extraction unit 302 according to the third example embodiment, and the time difference calculation unit 303 (FIG. 10). The information identification unit 403 is achieved by functions similar to the functions included in the information identification unit 103 (FIG. 1) according to the first example embodiment, the information identification unit 203 (FIG. 7) according to the second example embodiment, or the information identification unit 304 (FIG. 10) according to the third example embodiment.

When information relating to a pulse wave is factor information, the generation unit 402 generates factor information by executing processing similar to the processing described above in the first example embodiment (or the second example embodiment) between step S402 (described later with reference to FIG. 15) and step S403. In step S404, the information identification unit 403 identifies identification information by executing processing similar to the processing described above in the first example embodiment (or the second example embodiment). When information relating to a pulse wave is time difference information representing a time difference, identification information is determined based on pulse-wave information in accordance with processing (FIG. 11) described above in the third example embodiment.

Hereinafter, for convenience of description, it is assumed that information relating to a pulse wave is pulse-wave information.

Next, an operation in the identification device 401 according to the fourth example embodiment of the present invention is described in detail with reference to FIG. 15. FIG. 15 is a flowchart illustrating an operation in the identification device 401 according to the fourth example embodiment.

The control unit 404 starts measurement of a pulse wave of a biological subject, and control of pressure in accordance with a predetermined pressure control procedure (step S401). The control unit 404 controls the pulse-wave measurement unit 410 in such a way as to measure a pulse wave of a biological subject (or an identification target), and further controls the pump 405 in such a way as to control internal pressure of the cuff 411 in accordance with a predetermined pressure control procedure. In other words, the control unit 404 controls the pulse-wave measurement unit 410 in such a way as to measure a pulse wave of a biological subject (or an identification target) in a period in which the pump 405 is controlled in accordance with a predetermined pressure control procedure.

Thereafter, the control unit 404 finishes the measurement of the pulse wave of the biological subject, and the control of pressure in accordance with the predetermined pressure control procedure (step S402).

Next, the information identification unit 403 selects, from list information stored in the list information storage unit 412, pulse-wave information in which pulse-wave information in the list information and pulse-wave information representing a measured pulse wave satisfy a predetermined determination criterion (step S403). The information identification unit 403 identifies identification information representing an identifier included in list information relating to the selected pulse-wave information (step S404).

The identification device 401 may be a wearable-type device attached to a wrist. Moreover, the identification device 401 may be combined with an authentication system based on a face image, or an authentication system based on a fingerprint. Alternatively, the identification device 401 may be combined with an authentication system based on a password previously registered by a user. An authentication system based on a password represents, for example, a system which asks a user a question to which the user knows an answer, and authenticates the user, based on whether the answer is correct. A password may be one word, or may be a plurality of words. One example of processing when the identification device 401 is used in combination with an authentication system based on a password is specifically described.

For example, a user previously registers, on an authentication system, information representing a question to which the user himself/herself knows an answer. When authenticating with an authentication system, the user previously attaches the pulse-wave measurement unit 410 in the identification device 401 to a predetermined part, and starts utilization of the authentication system. The pulse-wave measurement unit 410 starts measurement of a pulse wave in accordance with processing as described with reference to FIG. 15. In a period in which the identification device 401 is measuring a pulse wave of the user, the authentication system displays, to the user, a question registered in the local system. The user inputs, to the authentication system, an answer to the question. After the authentication system receives the answer, the pulse-wave measurement unit 410 finishes the operation of measuring the pulse wave. In the identification device 401, the information identification unit 403 identifies identification information representing an identifier representing a user, in accordance with processing illustrated in FIG. 15 and the like, based on pulse-wave information representing a pulse wave measured by the pulse-wave measurement unit 410. The authentication system determines whether the received answer is correct. When the answer is correct, and the identification device 401 identifies identification information, the authentication system determines that the user is a true user. When the answer is incorrect, or the authentication system is not able to identify identification information, the authentication system determines that the user is a false user.

A system combining an authentication system based on a password with the identification device 401 can more firmly perform authentication. A reason for this is described. A user can keep his/her mind as usual when knowing a password. In this case, blood vessels of the user do not contract in response to a question from the authentication system. Therefore, when measuring a pulse wave of the user, the identification device 401 measures a pulse wave having a waveform similar to that of a pulse wave registered on the system, and thus, the authentication system determines that the user is a true user. In contrast, a user is mostly not able to keep his/her mind as usual when not knowing a password. In this case, blood vessels of the user contract in response to a question which the authentication system asks. Therefore, when the identification device 401 measures a pulse wave of the user, a pulse wave having a waveform similar to that of a pulse wave registered on the system is unlikely to be measured. As described in each of the above-described example embodiments, a pulse wave measured in a user is different from a pulse wave measured in a true user, and moreover, is different from a pulse wave of the user (in this case, a false user) himself/herself. In this case, the identification device 401 neither identifies identification information representing an identifier of the true user, nor identifies identification information representing an identifier of the false user himself/herself. Since the identification device 401 does not identify identification information of a true user, the authentication system determines that the user is a false user.

Another system may be a system combining a lie detector and the identification device 401. In this case, the identification device 401 measures a pulse wave for each question executed by the lie detector. When the identification device 401 does not identify identification information, the system determines that an answer to the question is a lie. Moreover, when the identification device 401 identifies identification information, the system determines that an answer to the question is correct.

Next, an effect relating to the identification device 401 according to the fourth example embodiment of the present invention is described.

The identification device 401 according to the fourth example embodiment can correctly identify a biological subject. A reason for this is similar to the reason described in the first example embodiment, or the reason described in the third example embodiment.

Furthermore, the identification device 401 according to the fourth example embodiment can provide information being a basis for building a more robust authentication system. A reason for this is that a pulse wave measured in a period in which external pressure is applied to blood vessels of a user has a waveform differing from that of a pulse wave measured in a period in which external pressure is not applied to the blood vessels, and the identification device 401 identifies a biological subject, based on the two pulse waves.

In addition, information being a basis for building an even more robust authentication system can be provided by controlling pressure in accordance with a predetermined pressure control procedure. A reason for this is that a waveform of a pulse wave measured in a user also changes as strength of external pressure applied to blood vessels in accordance with the predetermined pressure control procedure changes. For example, when pressure applied to blood vessels is controlled in accordance with the predetermined pressure control procedure, information representing hardness of the blood vessels more significantly appears in a pulse wave, and therefore, the identification device 401 can provide information being a basis for building an even more robust authentication system.

Hardware Configuration Example

A configuration example of a hardware resource which achieves the identification device according to each of the above-described example embodiments of the present invention by use of one calculation processing device (information processing device, computer) is described. However, the identification device may be physically or functionally achieved by use of at least two calculation processing devices. Moreover, the identification device may be achieved as a dedicated device.

Figure 16:
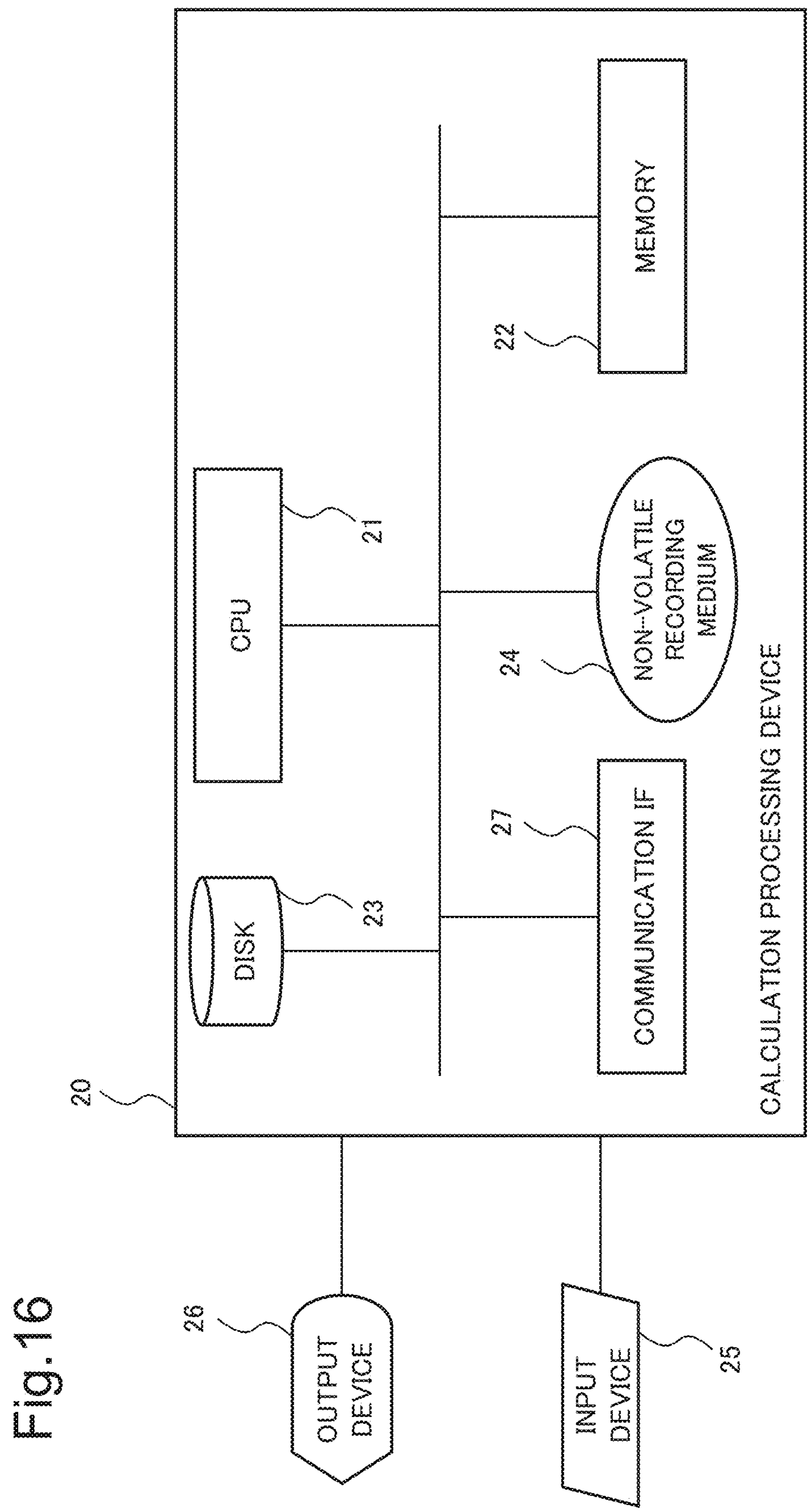
FIG. 16 is a block diagram schematically illustrating a hardware configuration example of a calculation processing device being capable of achieving the identification device according to each example embodiment of the present invention.

FIG. 16 is a block diagram schematically illustrating a hardware configuration example of a calculation processing device being capable of achieving the identification device according to each example embodiment of the present invention. A calculation processing device 20 includes a central processing unit (hereinafter, represented as a "CPU") 21, a memory 22, a disk 23, a non-volatile recording medium 24, and a communication interface (hereinafter, represented as a "communication IF") 27. The calculation processing device 20 may be connectable to an input device 25 and an output device 26. The calculation processing device 20 can transmit and receive information to and from another calculation processing device and a communication device via the communication IF 27.

The non-volatile recording medium 24 is, for example, a compact disc or a digital versatile disc that is computer-readable. Moreover, the non-volatile recording medium 24 may be a universal serial bus memory (USB memory), a solid state drive, or the like. The non-volatile recording medium 24 enables holding and carrying the program without supplying electric power. The non-volatile recording medium 24 is not limited to the medium described above. Moreover, the program may be carried via the communication IF 27 and a communication network instead of the non-volatile recording medium 24.

In other words, when executing a software program (computer program: hereinafter, simply referred to as a "program") stored in the disk 23, the CPU 21 copies the program into the memory 22, and executes calculation processing. The CPU 21 reads, from the memory 22, data required for program execution. When display is required, the CPU 21 displays an output result on the output device 26. When externally inputting a program, the CPU 21 reads the program from the input device 25. The CPU 21 interprets and executes an identification program (FIG. 2, 8, 11, or 15) being present in the memory 22 in places related to a function represented by each of the parts illustrated in FIGS. 1, 7, and 10 described above, or a function (processing) represented by the generation unit 402, the information identification unit 403, and the control unit 404 illustrated in FIG. 14. The CPU 21 sequentially executes processing described in each of the above-described example embodiments of the present invention.

In other words, in such a case, it can be comprehended that each example embodiment of the present invention can also be achieved by the identification program. Further, it can be comprehended that each example embodiment of the present invention can also be achieved by a computer-readable non-volatile recording medium recording the identification program.

The present invention has been described above with the above-described example embodiments as exemplary examples. However, the present invention is not limited to the above-described example embodiments. In other words, various aspects that can be understood by a person skilled in the art are applicable to the present invention within the scope of the present invention.

REFERENCE SIGNS LIST

101 Identification device
102 Generation unit
103 Information identification unit
150 List information storage unit
31 Timing
32 Timing
33 Timing
34 Timing
35 Timing
36 Timing
37 Timing
41 Timing
42 Timing
43 Timing
151 Factor information
152 Factor information
153 Factor information
160 Curve
161 Curve
162 Curve
201 Identification device
202 Filter processing unit
203 Information identification unit

211 Pulse-wave measurement unit
212 Environment information obtainment unit
213 Display unit
214 Biological information storage unit
301 Identification device
302 Wave extraction unit
303 Time difference calculation unit
304 Information identification unit
305 List information storage unit
351 Heart
352 Bifurcation
353 Bifurcation
354 Bifurcation
361 Curve
362 Timing
363 Timing
364 Timing
365 Timing
366 Timing
401 Identification device
402 Generation unit
403 Information identification unit
404 Control unit
405 Pump
410 Pulse-wave measurement unit
411 Cuff
412 List information storage unit
20 Calculation processing device
21 CPU
22 Memory
23 Disk
24 Non-volatile recording medium
25 Input device
26 Output device
27 Communication IF

What is claimed is:

1. An identification device comprising:

at least one memory storing instructions; and at least one processor connected to the at least one memory and configured to execute the instructions to:

measure pulse-wave information;

generate factor information by using the measured pulse-wave information and estimated pulse-wave information; and identify an identification target based on the generated factor information, wherein the at least one processor is configured to execute the instructions to calculate the estimated pulse-wave information based on biological model information represented by equation 1 and equation 2, wherein the equation 1 is expressed by $$X_t=(x_t,\theta_t)=g(x_{t-1},\theta_t)+v_t, \text{ and}$$

the equation 2 is expressed by $$y_t=h(x_t)+w_t, \text{ wherein}$$

t represents a timing, $x_t$ represents a state of the biological subject at a timing t, $y_t$ represents measurement information measured in relation to the identification target, $\theta_t$ represents a value of a parameter used in calculating a state at the timing t from a state at a timing (t−1), $v_t$ represents an error relating to process g, and $w_t$ represents an error relating to process h.

2. The identification device according to claim 1, wherein the factor information is a parameter that expresses a relationship between states of an biological subject at a plurality of timings.

3. The identification device according to claim 1, wherein the process g in the equation 1 represents a process of finding a state at a second timing from a state at a first timing, and the at least one processor is configured to execute the instructions to generate the factor information based on the value of the parameter $\theta_t$ in the equation 1.

4. The identification device according to claim 3, wherein the process g in the equation 1 is a process of solving equation 3 with respect to a variable x, wherein the equation 3 is expressed by $$m\frac{d^2x}{dt^2}=-kx-c\frac{dx}{dt}+F,$$

wherein m represents a volume of blood flow, k represents blood vessel resistance, c represents blood viscosity, F represents force applied to the blood vessels.

5. The identification device according to claim 1, wherein the factor information is information regarding a change in blood inside blood vessels of the identification target.

6. The identification device according to claim 1, wherein the factor information is at least one of parameters calculated according to a model estimation process, in which a value of the parameter $\theta_t$ is obtained for each of a plurality of timings according to a data assimilation process to reduce an error between the measurement information $y_t$ calculated according to the processes g and h of the equations 1 and 2 and the measured pulse-wave information, and the at least one processor is configured to execute the instructions to:

calculate the value of the parameter $\theta_t$, as the factor information, in accordance with the data assimilation process, along with the model estimation process acquired in relation to each timing so as to reduce the error between the measurement information $y_t$ calculated according to the processes g and h of the equations 1 and 2, and the measured pulse-wave information;

select certain list information satisfying a predetermined determination criterion of the generated factor information out of list information associating the factor information of the biological subject to be the identification target with identification information for identifying the biological subject; and identify the identification information in the selected certain list information.

7. The identification device according to claim 6, wherein the list information includes information representing a kind of medicine taken at measuring of the pulse wave of the biological subject, and the at least one processor is configured to execute the instructions to identify the certain list information based on information representing a kind of medicine taken by the identification target and the generated factor information.

8. The identification device according to claim 6, wherein the list information includes information representing a volume of water taken at measuring of the pulse wave of the biological subject, and the at least one processor is configured to execute the instructions to identify the certain list information based on information representing a volume of water taken by the identification target and the generated factor information.

9. The identification device according to claim 6, wherein the list information includes information representing a movement of the biological subject at measuring of the pulse wave of the biological subject, and the at least one processor is configured to execute the instructions to identify the certain list information based on information representing a movement of the identification target and the generated factor information.

10. The identification device according to claim 6, wherein the factor information in the list information is generated for the pulse-wave information measured during pressuring of the biological subject, and the measured pulse-wave information for the identification target is measured during pressuring of the identification target.

11. An identification device comprising:

at least one memory storing instructions; and at least one processor connected to the at least one memory and configured to execute the instructions to:

measure pulse-wave information; generate factor information based on an ejection wave included in the pulse-wave information and a reflected wave corresponding to the ejection wave; and identify an identification target based on the generated factor information, wherein the at least one processor is configured to execute the instructions to calculate the estimated pulse-wave information based on biological model information represented by equation 1 and equation 2, wherein the equation 1 is expressed by $X_t=(x_t,\theta_t)=g(x_{t-1},\theta_t)+v_t$, and the equation 2 is expressed by $y_t=h(x_t)+w_t$, wherein t represents a timing, xt represents a state of the biological subject at a timing t, yt represents measurement information measured in relation to the identification target, θt represents a value of a parameter used in calculating a state at the timing t from a state at a timing (t−1), vt represents an error relating to process g, and wt represents an error relating to process h.

12. The identification device according to claim 11, wherein the factor information is time difference information representing a time difference between the ejection wave and the reflected wave.

13. A non-transitory recording medium storing a program for causing a computer to execute processing of:

measuring pulse-wave information;

generating factor information by using the measured pulse-wave information and estimated pulse-wave information;

identifying an identification target based on the generated factor information; and calculating the estimated pulse-wave information based on biological model information represented by equation 1 and equation 2, wherein the equation 1 is expressed by $X_t=(x_t,\theta_t)=g(x_{t-1},\theta_t)+v_t$, and the equation 2 is expressed by $y_t=h(x_t)+w_t$, wherein t represents a timing, $x_t$ represents a state of the biological subject at a timing t, $y_t$ represents measurement information measured in relation to the identification target, $\theta_t$ represents a value of a parameter used in calculating a state at the timing t from a state at a timing (t−1), $v_t$ represents an error relating to process g, and $w_t$ represents an error relating to process h.

* * * * *